US009206161B2

(12) United States Patent
Singh et al.

(10) Patent No.: US 9,206,161 B2
(45) Date of Patent: Dec. 8, 2015

(54) BRIDGED BICYCLIC HETEROARYL SUBSTITUTED TRIAZOLES USEFUL AS AXL INHIBITORS

(71) Applicant: Rigel Pharmaceuticals, Inc., South San Francisco, CA (US)

(72) Inventors: Rajinder Singh, Belmont, CA (US); Sacha Holland, San Francisco, CA (US); Joane Litvak, Oakland, CA (US); Dane Goff, Redwood City, CA (US); Jing Zhang, Foster City, CA (US); Thilo J. Heckrodt, San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 14/593,981

(22) Filed: Jan. 9, 2015

(65) Prior Publication Data

US 2015/0126514 A1    May 7, 2015

Related U.S. Application Data

(62) Division of application No. 14/150,401, filed on Jan. 8, 2014, now Pat. No. 8,933,080, which is a division of application No. 13/620,010, filed on Sep. 14, 2012, now Pat. No. 8,658,669, which is a division of application No. 13/002,488, filed as application No. PCT/US2009/049627 on Jul. 2, 2009, now Pat. No. 8,431,594.

(60) Provisional application No. 61/079,398, filed on Jul. 9, 2008.

(51) Int. Cl.
| | | |
|---|---|---|
| *A61K 31/502* | (2006.01) |
| *C07D 403/04* | (2006.01) |
| *C07D 401/14* | (2006.01) |
| *C07D 403/14* | (2006.01) |
| *C07D 471/18* | (2006.01) |
| *C07D 221/22* | (2006.01) |
| *C07D 237/26* | (2006.01) |
| *C07D 237/34* | (2006.01) |

(52) U.S. Cl.
CPC ............ *C07D 403/04* (2013.01); *C07D 221/22* (2013.01); *C07D 237/26* (2013.01); *C07D 401/14* (2013.01); *C07D 403/14* (2013.01); *C07D 471/18* (2013.01); *A61K 31/502* (2013.01); *C07D 237/34* (2013.01)

(58) Field of Classification Search
CPC ..................... C07D 403/14; A61K 31/498
See application file for complete search history.

(56) References Cited

U.S. PATENT DOCUMENTS

| | | | |
|---|---|---|---|
| 3,813,400 A | 5/1974 | Boyle et al. | |
| 6,924,302 B2 | 8/2005 | Lin et al. | |
| 7,709,482 B2 * | 5/2010 | Goff et al. ...................... 514/248 |
| 7,872,000 B2 | 1/2011 | Goff et al. | |
| 7,879,856 B2 | 2/2011 | Goff et al. | |
| 7,884,119 B2 | 2/2011 | Singh et al. | |
| 7,935,693 B2 | 5/2011 | Singh et al. | |
| 8,012,965 B2 | 9/2011 | Goff et al. | |
| 8,097,630 B2 | 1/2012 | Singh et al. | |
| 8,168,636 B2 | 5/2012 | Goff et al. | |
| 8,288,382 B2 | 10/2012 | Goff et al. | |
| 8,309,566 B2 | 11/2012 | Bhamidipati et al. | |
| 8,349,838 B2 | 1/2013 | Singh et al. | |
| 8,389,557 B2 | 3/2013 | Singh et al. | |
| 8,431,594 B2 * | 4/2013 | Singh et al. .................... 514/300 |
| 8,492,373 B2 | 7/2013 | Goff et al. | |
| 8,563,559 B2 | 10/2013 | Singh et al. | |
| 8,609,650 B2 | 12/2013 | Goff et al. | |
| 8,618,331 B2 | 12/2013 | Goff et al. | |
| 8,658,669 B2 * | 2/2014 | Singh et al. .................... 514/300 |
| 8,735,418 B2 | 5/2014 | Bhamidipati et al. | |
| 8,741,898 B2 | 6/2014 | Goff et al. | |
| 8,796,259 B2 | 8/2014 | Ding et al. | |
| 8,809,347 B2 | 8/2014 | Goff et al. | |
| 8,809,364 B2 | 8/2014 | Singh et al. | |
| 8,906,922 B2 | 12/2014 | Goff et al. | |
| 8,933,080 B2 * | 1/2015 | Singh et al. .............. 514/252.03 |
| 2004/0077699 A1 | 4/2004 | Lin et al. | |
| 2004/0186288 A1 | 9/2004 | Kruger et al. | |
| 2004/0214817 A1 | 10/2004 | Pierce et al. | |

(Continued)

FOREIGN PATENT DOCUMENTS

| | | |
|---|---|---|
| EP | 0 710 654 A1 | 5/1996 |
| WO | WO 01/09106 A1 | 2/2001 |
| WO | WO 02/57240 A1 | 7/2002 |
| WO | WO 02/94814 A1 | 11/2002 |
| WO | WO 03/027275 A1 | 4/2003 |
| WO | WO 03/093344 A1 | 11/2003 |
| WO | WO 2004/017997 A1 | 3/2004 |
| WO | WO 2004/039955 A2 | 5/2004 |
| WO | WO 2004/046120 A2 | 6/2004 |
| WO | WO 2005/013982 A1 | 2/2005 |

(Continued)

OTHER PUBLICATIONS

J.P. O'Bryan et al., 11 Molecular and Cell Biology, 5016-5031 (1991).*

(Continued)

*Primary Examiner* — Alexander R Pagano
(74) *Attorney, Agent, or Firm* — Seed IP Law Group PLLC; Travis Young

(57) ABSTRACT

Bridged bicyclic heteroaryl substituted triazoles and pharmaceutical compositions containing the compounds are disclosed as being useful in inhibiting the activity of the receptor protein tyrosine kinase Axl. Methods of using the compounds in treating diseases or conditions associated with Axl activity are also disclosed.

5 Claims, No Drawings

(56) References Cited

U.S. PATENT DOCUMENTS

| | | | |
|---|---|---|---|
| 2005/0118604 | A1 | 6/2005 | Lorens et al. |
| 2006/0293256 | A1 | 12/2006 | Yamada et al. |
| 2008/0182862 | A1 | 7/2008 | Ding et al. |
| 2010/0196511 | A1 | 8/2010 | Hitoshi et al. |
| 2013/0109695 | A1 | 5/2013 | Singh et al. |
| 2013/0338161 | A1 | 12/2013 | Hitoshi et al. |
| 2014/0155386 | A1 | 6/2014 | Goff et al. |
| 2014/0213585 | A1 | 7/2014 | Bhamidipati et al. |
| 2014/0323490 | A1 | 10/2014 | Goff et al. |
| 2015/0072959 | A1 | 3/2015 | Goff et al. |

FOREIGN PATENT DOCUMENTS

| | | | |
|---|---|---|---|
| WO | WO 2005/077922 | A2 | 8/2005 |
| WO | WO 2006/034116 | A1 | 3/2006 |
| WO | WO 2006/047256 | A1 | 5/2006 |
| WO | WO 2006/050249 | A1 | 5/2006 |
| WO | WO 2008/083353 | A1 | 7/2008 |
| WO | WO 2008/083357 | A1 | 7/2008 |
| WO | WO 2008/157131 | A1 | 12/2008 |
| WO | WO 2009/054864 | A1 | 4/2009 |
| WO | WO 2010/005876 | A2 | 1/2010 |

OTHER PUBLICATIONS

P.R. van Ginkel et al., 64 Cancer Research, 128-134, 128 (2004).*
S.J. Holland et al., 70 Cancer Research, 1544-1554, 1544 (2010).*
F. Bunz, Principles of Cancer Genetics 1-47, 1 (2008).*
P.K. Kuppen et al., 115 Histochemistry and Cell Biology, 67-72 (2001).*
J. Luo et al., 36 Cell, 823-837 (2009); T. Soussi 60 Cancer Research, 1777-1788 (2000).*
P. Lissoni et al, 7 Cancer Research, 397-401 (2009).*
National Cancer Institute (http://www.cancer.gov/) (Downloaded May 29, 2014).*
H.A. Fine, Neoplasms of the Central Nervous System in, 2 Cancer Principles & Practice of Oncology 1834-1887 (V.T. DeVita, Jr. et al. eds., 5th ed., 2005).*
L.I. Zon et al., Nature Reviews Drug Discovery 4, 35 (2005).*
A. Kamb, Nature Reviews Drug Discovery 2, 161-165 (2005).*
K-Y Tai, 27 Oncogene, 4044-4055 (2008).*
J.H. Poupaert, Drug Design: Basic Principles and Applications, in 2 Encyclopedia of Pharmaceutical Technology 1362-1369, 1367 (James Swarbrick ed., 3rd ed., 2007).*
Reiter and Pongó, "On Triazoles. On Triazoles. VI [1]. The Acylation of 5-Amino-1,2,4Triazoles," *J. Heterocyclic Chem.* 24(1): 127-142, Jan.-Feb. 1987.
Sarayba et al , "Inhibition of corneal neovascularization by a peroxisome proliferator-activated receptor-γ ligand," *Experimental Eye Research 80*: 435-442, 2005.
Agrafiotis et al., "SAR Maps: A New SAR Visualization Technique for Medicinal Chemists," *J. Med. Chem.* 50(24): 5926-5937, 2007.
Alexander et al., "Human Parathyroid Hormone 1-34 Reverses Bone Loss in Ovariectomized Mice," *Journal of Bone and Mineral Research* 16(9): 1665-1673, 2001.
Angelillo-Scherrer et al., "Role of Gas6 receptors in platelet signaling during thrombus stabilization and implications for antithrombotic therapy," *Journal of Clinical Investigation* 115(2): 237-246, Feb. 2005.
Arterburn et al., "Catalytic Amination of 2-Substituted Pyridines with Hydrazine Derivatives," *Organic Letters* 3(9): 1351-1354, Feb. 20, 2001.
Bora et al., "Immunotherapy for choroidal neovascularization in a laser-induced mouse model simulating exudative (wet) macular degeneration," *Proc. Natl. Acad. Sci U.S.A.* 100(5): 2679-2684, Mar. 4, 2003.
Brewster et al., "Ro 32/3555, an orally active collagenase selective inhibitor, prevents structural damage in the STR/ORT mouse model of osteoarthritis," *Arthritis & Rheumatism* 41(9): 1639-1644, Sep. 1998.

Chen et al., "Chapter 33—How Melanoma Cells Evade Chemotherapy: Role of Transporter-Dependent and —Independent Resistance Mechanisms," *From Melanocytes to Melanoma: The Progression to Malignancy*, V. J. Hearing et al. editors, Humana Press Inc., Totowa, New Jersey, pp. 591-603, 2006.
Fujioka et al., "Equol, a Metabolite of Daidzein, Inhibits Bone Loss in Ovariectomized Mice," *Journal of Nutrition* 134: 2623-2627, 2004.
Hann et al., "Building 'validated' mouse models of human cancer," *Current Opinion in Cell Biology* 13: 778-784, 2001.
Holland et al., "Multiple Roles for the Receptor Tyrosine Kinase Axl in Tumor Formation," *Cancer Res.* 65(20): 9294-9303, Oct. 15, 2005.
Holland et al., "Requirement for the Receptor Tyrosine Kinase Axl in Angiogenesis and Tumor Growth", 7th Annual Symposium on Anti-Angiogenic Agents, Feb. 10-13, 2005, San Diego, California, 1 page.
Kadoya et al., "Role of calpain in hydrogen peroxide induced cataract," *Current Eye Research* 12(4): 341-346, 1993.
Katritzky et al., "Syntheses of 5-(2-arylazenyl)-1,2,4-triazoles and 2-amino-5-aryl-1,3,4oxadiazoles," *ARKIVOC* 6: 82-90, 2002.
Kim et al., "Novel Oral Formulation of Paclitaxel Inhibits Neointimal Hyperplasia in a Rat Carotid Artery Injury Model," *Circulation* 109(12): 1558-1563, Mar. 8, 2004.
Kurzer and Douraghi-Zadeh, "Heterocyclic Compounds from Urea Derivatives. Part VI. Synthesis and Cyclisation of 1-Amino-3-(NN'-diarylamidino)guanidines and Some Analogues," *J. Chem. Soc.* 932-937, 1965.
Lebovic et al., "Peroxisome proliferator-activated receptor-gamma induces regression of endometrial explants in a rat model of endometriosis," *Fertility and Sterility* 82(Suppl 3): 1008-1013, Oct. 2004.
Nakashima et al., "ApoE-Deficient Mice Develop Lesions of All Phases of Atherosclerosis Throughout the Arterial Tree," *Arterioscler. Thromb. Vasc. Biol.* 14(1): 133-140, Jan. 1994.
Nickoloff et al., "Severe Combined Immunodeficiency Mouse and Human Psoriatic Skin Chimeras. Validation of a New Animal Model," *American Journal of Pathology* 146(3): 580-588, Mar. 1995.
O'Bryan et al., "*Axl*, a Transforming Gene Isolated from Primary Human Myeloid Leukemia Cells, Encodes a Novel Receptor Tyrosine Kinase," *Molecular and Cellular Biology* 11(10): 5016-5031, Oct. 1991.
Olive et al., "The Use of Targeted Mouse Models for Preclinical Testing of Novel Cancer Therapeutics," *Clin. Cancer Res.* 12(18): 5277-5287, Sep. 15, 2006.
Patani and LaVoie, "Bioisosterism: A Rational Approach in Drug Design," *Chem. Rev* 96: 3147-3176, 1996.
Phadke et al., "Evaluation of the Effects of Various Anti-Arthritic Drugs on Type II Collagen-Induced Mouse Arthritis Model," *Immunopharmacology* 10: 51-60, 1985.
Reiter and Pongó, "On Triazoles. On Triazoles. VI [1]. The Acylation of 5-Amino-1,2,4-Triazoles," *J. Heterocyclic Chem.* 24(1): 127-142, Jan-Feb 1987.
Sarayba et al., "Inhibition of corneal neovascularization by a peroxisome proliferator-activated receptor-γ ligand," *Experimental Eye Research 80*: 435-442, 2005.
Sharpless et al., "The mighty mouse: genetically engineered mouse models in cancer drug development," *Nature Reviews—Drug Discovery*, pp. 1-14, 2006.
Sheets et al., "Cataract- and Lens-Specific Upregulation of ARK Receptor Tyrosine Kinase in Emory Mouse Cataract," *Investigative Ophthalmology & Visual Science* 43(6): 1870-1875, Jun. 2002.
Smith et al., "Oxygen-Induced Retinopathy in the Mouse," *Investigative Ophthalmology & Visual Science* 35(1): 101-111, Jan. 1994.
Somigliana et al., "Endometrial ability to implant in ectopic sites can be prevented by interleukin-12 in a murine model of endometriosis," *Human Reproduction* 14(12): 2944-2950, 1999.
Traynor et al., "Systemic Treatment of Advanced Non-Small Cell Lung Cancer," *Drugs of Today* 40(8): 697-710, 2004.
Van Ginkel et al., "Expression of the Receptor Tyrosine Kinase Axl Promotes Ocular Melanoma Cell Survival," *Cancer Research* 64: 128-134, Jan. 1, 2004.
Veljkovic et al., "Application of the EIIP/ISM Bioinformatics Concept in Development of New Drugs," *Current Medicinal Chemistry* 14: 441-453, 2007.

(56) References Cited

OTHER PUBLICATIONS

Von Der Thüsen et al., "Adenoviral Transfer of Endothelial Nitric Oxide Synthase Attenuates Lesion Formation in a Novel Murine Model of Postangioplasty Restenosis," *Arterioscler. Thromb. Vasc. Biol. 24*: 357-362, Feb. 2004.

Wronski et al., "Endocrine and Pharmacological Suppressors of Bone Turnover Protect against Osteopenia in Ovariectomized Rats," *Endocrinology 125*(2): 810-816, 1989.

Xu et al., "Requirement for the tyrosine kinase Axl in angiogenesis and tumor growth," *Proc. Amer. Assoc. Cancer Res. 46*, 2005. Tumor Biology 14: Signaling and Angiogenesis; Abstract #2019 of observations disclosed at American Association Cancer Research General Meeting, Apr. 16-20, 2005, Anaheim, California, 1 page.

Yin et al., "Expression of growth arrest-specific gene 6 and its receptors in a rat model of chronic renal transplant rejection," *Transplantation 73*(4): 657-660, Feb. 27, 2002.

\* cited by examiner

BRIDGED BICYCLIC HETEROARYL SUBSTITUTED TRIAZOLES USEFUL AS AXL INHIBITORS

CROSS-REFERENCE TO RELATED APPLICATIONS

This application is a divisional of U.S. patent application Ser. No. 14/150,401, filed Jan. 8, 2014 (now allowed); which is a divisional of U.S. patent application Ser. No. 13/620,010, filed Sep. 14, 2012 (now U.S. Pat. No. 8,658,669); which is a divisional application of U.S. patent application Ser. No. 13/002,488, filed Jan. 3, 2011 (now U.S. Pat. No. 8,431,594); which is a national stage application, filed under 35 U.S.C. §371, of International Application No. PCT/US2009/049627, accorded an international filing date of Jul. 2, 2009; which claims the benefit under 35 U.S.C. §119(e) of U.S. Provisional Patent Application No. 61/079,398, filed Jul. 9, 2008.

FIELD OF THE INVENTION

This invention is directed to bridged bicyclic heteroaryl substituted triazoles and pharmaceutical compositions thereof which are useful as inhibitors of the receptor protein tyrosine kinase known as Axl. This invention is also directed to methods of using the compounds and compositions in treating diseases and conditions associated with Axl activity, particularly in treating diseases and conditions associated with angiogenesis and/or cell proliferation.

BACKGROUND OF THE INVENTION

All of the protein kinases that have been identified to date in the human genome share a highly conserved catalytic domain of around 300 aa. This domain folds into a bi-lobed structure in which reside ATP-binding and catalytic sites. The complexity of protein kinase regulation allows many potential mechanisms of inhibition including competition with activating ligands, modulation of positive and negative regulators, interference with protein dimerization, and allosteric or competitive inhibition at the substrate or ATP binding sites.

Axl (also known as UFO, ARK, and Tyro7; nucleotide accession numbers NM_021913 and NM_001699; protein accession numbers NP_068713 and NP_001690) is a receptor protein tyrosine kinase (RTK) that comprises a C-terminal extracellular ligand-binding domain and N-terminal cytoplasmic region containing the catalytic domain. The extracellular domain of Axl has a unique structure that juxtaposes immunoglobulin and fibronectin Type III repeats and is reminiscent of the structure of neural cell adhesion molecules. Axl and its two close relatives, Mer/Nyk and Sky (Tyro3/Rse/Dtk), collectively known as the Tyro3 family of RTK's, all bind and are stimulated to varying degrees by the same ligand, Gas6 (growth arrest specific-6), a ~76 kDa secreted protein with significant homology to the coagulation cascade regulator, Protein S. In addition to binding to ligands, the Axl extracellular domain has been shown to undergo homophilic interactions that mediate cell aggregation, suggesting that one important function of Axl may be to mediate cell-cell adhesion.

Axl is predominantly expressed in the vasculature in both endothelial cells (EC's) and vascular smooth muscle cells (VSMC's) and in cells of the myeloid lineage and is also detected in breast epithelial cells, chondrocytes, Sertoli cells and neurons. Several functions including protection from apoptosis induced by serum starvation, TNF-α or the viral protein E1A, as well as migration and cell differentiation have been ascribed to Axl signaling in cell culture. However, Axl−/− mice exhibit no overt developmental phenotype and the physiological function of Axl in vivo is not clearly established in the literature.

Angiogenesis (the formation of new blood vessels) is limited to functions such as wound healing and the female reproductive cycle in healthy adults. This physiological process has been co-opted by tumors, thus securing an adequate blood supply that feeds tumor growth and facilitates metastasis. Deregulated angiogenesis also a feature of many other diseases (for example, psoriasis, rheumatoid arthritis, endometriosis and blindness due to age-related macular degeneration (AMD), retinopathy of prematurity and diabetes) and often contributes to the progression or pathology of the condition.

The overexpression of Axl and/or its ligand has also been reported in a wide variety of solid tumor types including, but not limited to, breast, renal, endometrial, ovarian, thyroid, non-small cell lung carcinoma, and uveal melanoma as well as in myeloid leukemia's. Furthermore, it possesses transforming activity in NIH3T3 and 32D cells. It has been demonstrated that loss of Axl expression in tumor cells blocks the growth of solid human neoplasms in an in vivo MDA-MB-231 breast carcinoma xenograft model. Taken together, these data suggest Axl signaling can independently regulate EC angiogenesis and tumor growth and thus represents a novel target class for tumor therapeutic development.

The expression of Axl and Gas6 proteins is upregulated in a variety of other disease states including endometriosis, vascular injury and kidney disease and Axl signaling is functionally implicated in the latter two indications. Axl-Gas6 signaling amplifies platelet responses and is implicated in thrombus formation. Axl may thus potentially represent a therapeutic target for a number of diverse pathological conditions including solid tumors, including, but not limited to, breast, renal, endometrial, ovarian, thyroid, non-small cell lung carcinoma and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoporosis, osteoarthritis and cataracts.

SUMMARY OF THE INVENTION

This invention is directed to certain bridged bicyclic heteroaryl substituted triazoles which are useful as Axl inhibitors, methods of using such compounds in treating diseases and conditions associated with Axl activity and pharmaceutical compositions comprising such compounds.

Accordingly, in one aspect this invention is directed to compounds of formula (I):

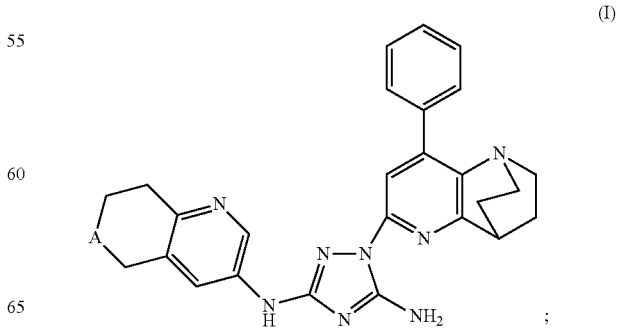

where:

A is —C(R¹)(H)— or —N(R²)—;

R¹ is selected from the group consisting of —N(R³)R⁴ and —N(R³)C(O)—R⁵—N(R³)R⁴;

R² is selected from the group consisting of hydrogen, cycloalkyl and —C(O)—R⁵—N(R³)R⁴; and each R³ and R⁴ is independently selected from the group consisting of hydrogen and alkyl;

as an isolated stereoisomer or a mixture thereof, or as a pharmaceutically acceptable salt thereof.

In another aspect, this invention is directed to compounds of formula (II):

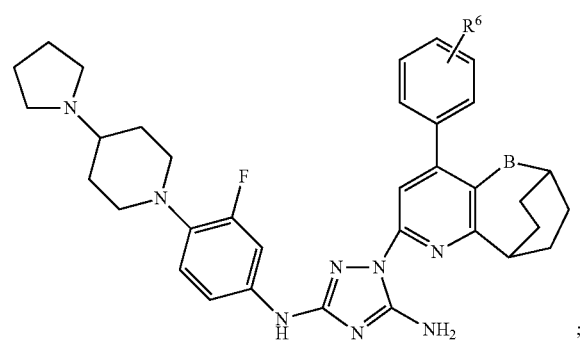

(II)

wherein:

B is a direct bond or —CH₂—; and

R⁶ is selected from the group consisting of hydrogen, halo, haloalkyl, alkoxy or alkyl;

as an isolated stereoisomer or a mixture thereof, or as a pharmaceutically acceptable salt thereof;

provided that the compound of formula (I) is not 1-(1,4-ethano-8-phenyl-1,2,3,4-tetrahydro-1,5-naphthyridin-6-yl)-N³-(3-fluoro-4-(4-(pyrrolidin-1-yl)piperidin-1-yl)phenyl)-1H-1,2,4-triazole-3,5-diamine.

In another aspect, this invention is directed to compounds of formula (III):

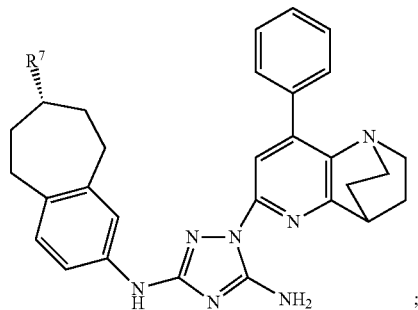

(III)

wherein:

R⁷ is selected from the group consisting of —N(R¹²)R¹³ and —N(R¹²)C(O)OR¹³; and each R¹² and R¹³ is selected from the group consisting of hydrogen, alkyl and cycloalkyl;

as an isolated stereoisomer or a mixture thereof, or as a pharmaceutically acceptable salt thereof.

In another aspect, this invention is directed to compounds of formula (IV):

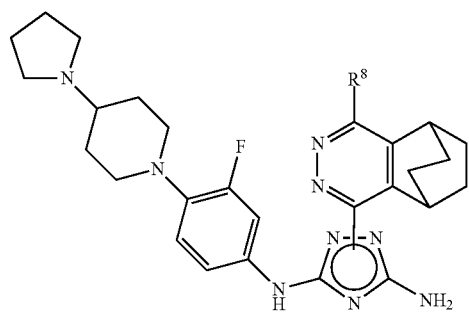

(IV)

wherein:

R⁹ is selected from the group consisting of halo, pyridinyl, benzodioxolyl and phenyl optionally substituted by a substituent selected from the group consisting of cyano and alkyl;

as an isolated stereoisomer or a mixture thereof, or as a pharmaceutically acceptable salt thereof.

In another aspect, this invention is directed to compounds of formula (V):

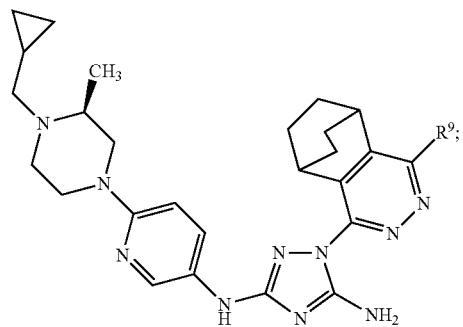

(V)

wherein:

R⁹ is selected from the group consisting of halo, pyridinyl and phenyl optionally substituted by a substituent selected from the group consisting of halo and alkyl;

as an isolated stereoisomer or a mixture thereof, or as a pharmaceutically acceptable salt thereof.

In another aspect, this invention is directed to compounds of formula (VI):

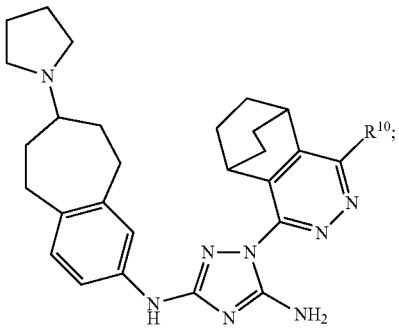

(VI)

wherein:

R¹⁰ is selected from the group consisting of halo, pyridinyl and phenyl optionally substituted by one or more substituents selected from the group consisting of halo, cyano, alkoxy and alkyl;

as an isolated stereoisomer or a mixture thereof, or as a pharmaceutically acceptable salt thereof.

In another aspect, this invention is directed to compounds of formula (VII):

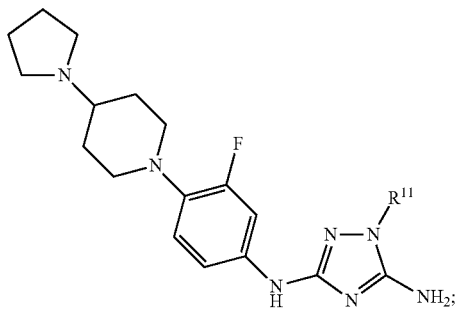

(VII)

wherein:
R[11] is selected from the group consisting of:

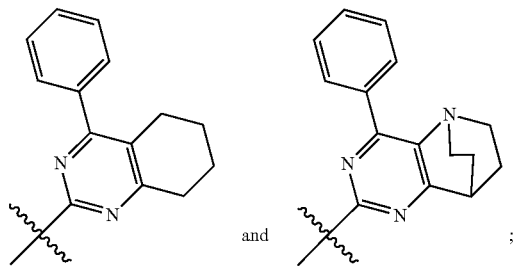 [SMILES: *c1nc2c(c(-c3ccccc3)n1)CCCC2 ; *c1nc(-c2ccccc2)c2c(n1)C1CCN2CC1]

as an isolated stereoisomer or a mixture thereof, or as a pharmaceutically acceptable salt thereof.

In another aspect, this invention is directed to pharmaceutical compositions comprising a pharmaceutically acceptable excipient and a compound of the invention, as described above, as an isolated stereoisomer or mixture thereof, or a pharmaceutically acceptable salt thereof.

In another aspect, this invention is directed to methods of treating a disease or condition associated with Axl activity in a mammal, wherein the methods comprise administering to the mammal a therapeutically effective amount of a compound of the invention, as described above, as an isolated stereoisomer or mixture thereof, or a pharmaceutically acceptable salt thereof, or a therapeutically effective amount of a pharmaceutical composition comprising a pharmaceutically acceptable excipient and a compound of the invention, as described above, as an isolated stereoisomer or mixture thereof, or a pharmaceutically acceptable salt thereof.

In another aspect, this invention provides assays to determine a compound of the invention effectiveness in inhibiting Axl activity in a cell-based assay.

In another aspect, this invention provides methods of preparing an (S)-enantiomer of the following formula:

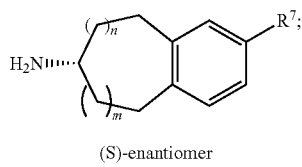

(S)-enantiomer where n and m are the same and are 0, 1 or 2;
R[7] is nitro, halo or —C(O)OR[2]; and
R[2] is hydrogen, alkyl, alkenyl, optionally substituted aralkyl, optionally substituted cycloalkyl, optionally substituted cycloalkylalkyl and optionally substituted heteroaryl;

wherein the method comprises treating a compound of formula (i):

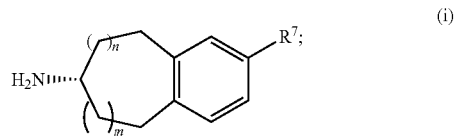

(i)

where n and m are the same and are 0, 1 or 2;
R[7] is nitro, halo or —C(O)OR[2]; and
R[2] is hydrogen, alkyl, alkenyl, optionally substituted aralkyl, optionally substituted cycloalkyl, optionally substituted cycloalkylalkyl and optionally substituted heteroaryl;
with an amino donor molecule in the presence of a catalytic amount of a (S)-specific transaminase under suitable conditions to form the (S)-enantiomer.

DETAILED DESCRIPTION OF THE INVENTION

Definitions

As used in the specification and appended claims, unless specified to the contrary, the following terms have the meaning indicated:

"Amino" refers to the —NH$_2$ radical.
"Carboxy" refers to the —C(O)OH radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms ("lower alkyl"), and which is attached to the rest of the molecule by a single bond, for example, methyl, ethyl, n-propyl, 1-methylethyl(iso-propyl), n-butyl, n-pentyl, 1,1-dimethylethyl(t-butyl), 3-methylhexyl, 2-methylhexyl, and the like.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain.

"Alkoxy" refers to a radical of the formula —OR$_a$ where R$_a$ is an alkyl radical as defined above containing one to twelve carbon atoms.

"Amino-donor molecule" refers to a organic molecule comprising a primary amine (—NH$_2$) group and which is suitable for the processes disclosed herein. Examples of amino-donor molecules include, but are not limited to, α-amino acids, such as alanine and phenylalanine, isopropylamine, 1-ethylpropylamine, 1,1,3,3-tetramethylbutylamine, 1,2-dimethylbutylamine, sec-butylamine, 1-phenylethylamine and the like.

"Cycloalkyl" refers to a stable non-aromatic monocyclic or polycyclic hydrocarbon radical consisting solely of carbon and hydrogen atoms, which may include spiro or bridged ring systems, having from three to fifteen carbon atoms, preferably having from three to ten carbon atoms, more preferably from five to seven carbons and which is saturated or unsaturated and attached to the rest of the molecule by a single bond. For purposes of this invention, a bridged ring system is a system wherein two non-adjacent ring atoms thereof are connected through an atom or a group of atoms. Monocyclic cycloalkyl radicals include non-bridged cycloalkyl radicals, for example, cyclopropyl, cyclobutyl, cyclopentyl, cyclohexyl, cycloheptyl, and cyclooctyl. Polycyclic radicals include fused, spiro or bridged cycloalkyl radicals, for example, $C_{10}$ radicals such as adamantanyl (bridged) and decalinyl (fused), and $C_7$ radicals such as bicyclo[3.2.0]heptanyl (fused), norbornanyl and norbornenyl (bridged), as well as substituted polycyclic radicals, for example, substituted $C_7$ radicals such as 7,7-dimethylbicyclo[2.2.1]heptanyl (bridged), and the like.

"Cycloalkylalkyl" refers to a radical of the formula —$R_bR_g$ where $R_b$ is an alkylene chain as defined above and $R_g$ is a cycloalkyl radical as defined above. The alkylene chain and the cycloalkyl radical may be optionally substituted as defined above.

"Enantiomeric excess" or "ee" refers to a product wherein one enantiomer is present in excess of the other, and is defined as the absolute difference in the mole fraction of each enantiomer. Enantiomeric excess is typically expressed as a percentage of an enantiomer present in a mixture relative to the other enantiomer. For purpose of this invention, the (S)-enantiomer of the invention is considered to be substantially free of the (R)-enantiomer when the (S)-enantiomer is present in enantiomeric excess of greater than 80%, preferably greater than 90%, more preferably greater than 95% and most preferably greater than 99%.

"Halo" refers to bromo, chloro, fluoro or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Keto acid" refers to a carboxylic acid additionally containing a ketone functional group. An "2-keto acid" refers to a carboxylic acid wherein the ketone functional group is adjacent to the carboxylic acid (—C(O)OH) group.

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like. Preferably, for purposes of this invention, the mammal is a human.

"Optional" or "optionally" means that the subsequently described event or circumstances may or may not occur, and that the description includes instances where said event or circumstance occurs and instances in which it does not. For example, "phenyl optionally substituted" means that the phenyl radical may or may not be substituted and that the description includes both substituted phenyl radicals and phenyl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfonic acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the invention and a medium generally accepted in the art for the delivery of the biologically active compound to mammals, for example, humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a disease or condition of interest in the mammal, preferably a human. The amount of a compound of the invention which constitutes a "therapeutically effective amount" will vary depending on the compound, the disease or condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

"Transaminases" as used herein refers to naturally occurring or non-natural enzymes which catalyze the transfer of an amino group from an amino donor molecule to a ketone-containing molecule, preferably to a cyclic ketone fused to an aromatic ring, to produce an optically active molecule. Transaminases, or aminotransferases, have high stereoselectivity for a given enantiomer. Thus, the process of transamination utilizing a transaminase is a chiral synthesis, not a resolution.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

The chemical naming protocol and structure diagrams used herein are a modified form of the I.U.P.A.C. nomenclature system wherein the compounds of the invention are named herein as derivatives of the central core structure, i.e., the triazole structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

For purposes of this invention, the depiction of the bond attaching the phthalazine moiety to the central diaminotriazole moiety in formula (IV), as shown below:

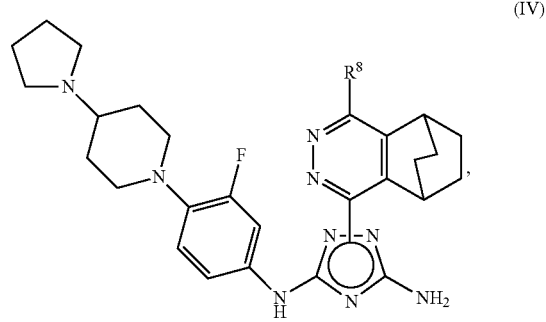

(IV)

is intended to include only the two regioisomers shown below, i.e., compounds of formula (IVa) and (IVb):

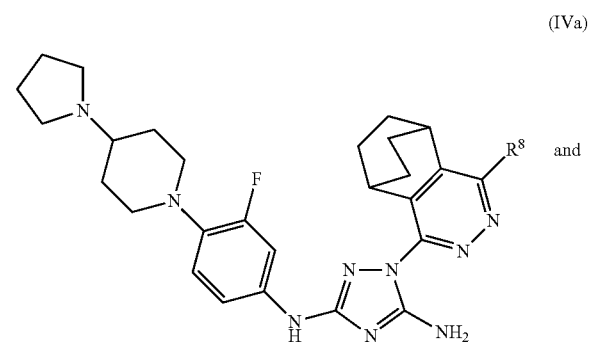

(IVa) and

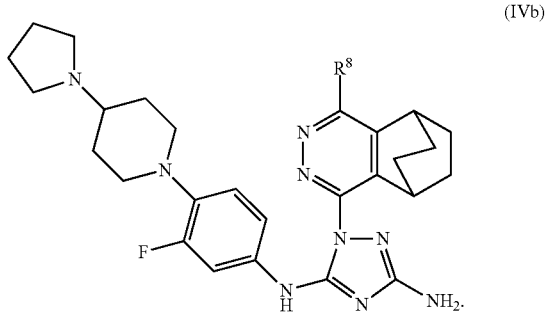

(IVb)

The numbering system of the diaminotriazole atoms in compounds of formula (IVa) is shown below:

(IVa)

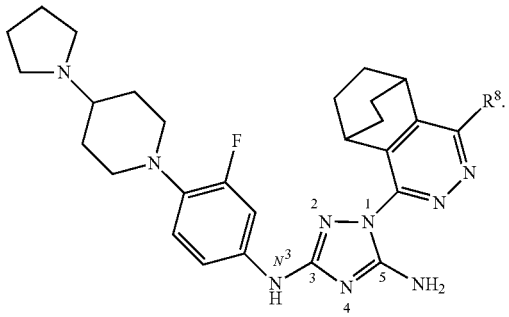

For example, a compound of formula (IVa) wherein $R^8$ is 2-chlorophenyl is named herein as 1-(4-(2-chlorophenyl)-5,8-ethano-5,6,7,8-tetrahydrophthalazine-1-yl)-$N^3$-(4-(4-(pyrrolidin-1-yl)piperidinyl)-3-fluorophenyl)-1H-1,2,4-triazole-3,5-diamine.

The numbering system of the ring atoms in compounds of formula (IVb) is shown below:

(IVb)

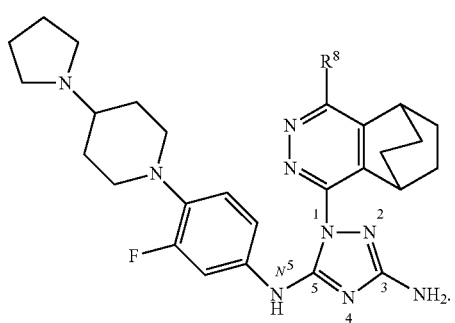

For example, a compound of formula (IVb) wherein $R^8$ is chloro is named herein as 1-(4-chloro-5,8-ethano-5,6,7,8-tetrahydrophthalazine-1-yl)-$N^5$-(4-(4-(pyrrolidin-1-yl)piperidinyl)-3-fluorophenyl)-1H-1,2,4-triazole-3,5-diamine.

Embodiments of the Invention

Of the various aspects of the compounds of the invention, as set forth above in the Summary of the Invention, certain embodiments are preferred.

One embodiment of the invention is a compound of formula (I), as set forth above in the Summary of the Invention, as an isolated stereoisomer or a mixture thereof, or as a pharmaceutically acceptable salt thereof.

Another embodiment of the invention is a compound of formula (I), as set forth above in the Summary of the Invention, having the following formula (Ia):

(Ia)

wherein:
$R^1$ is selected from the group consisting of —$N(R^3)R^4$ and —$N(R^3)C(O)$—$R^5$—$N(R^3)R^4$; and
each $R^3$ and $R^4$ is independently selected from the group consisting of hydrogen and alkyl;
as an isolated stereoisomer or a mixture thereof, or as a pharmaceutically acceptable salt thereof.

Another embodiment of the invention is a compound of formula (Ia), as set forth above, which is selected from the group consisting of:
1-(1,4-ethano-8-phenyl-1,2,3,4-tetrahydro-1,5-naphthyridin-6-yl)-$N^3$-(6-amino-5,6,7,8-tetrahydroquinoline-3-yl)-1H-1,2,4-triazole-3,5-diamine;
1-(1,4-ethano-8-phenyl-1,2,3,4-tetrahydro-1,5-naphthyridin-6-yl)-$N^3$-(6-[(((dimethyl)amino)methyl)carbonylamino]-5,6,7,8-tetrahydroquinoline-3-yl)-1H-1,2,4-triazole-3,5-diamine; and
1-(1,4-ethano-8-phenyl-1,2,3,4-tetrahydro-1,5-naphthyridin-6-yl)-$N^3$-(6-H-1,2,4-triazole-3,5-diamine,
as an isolated stereoisomer or a mixture thereof, or as a pharmaceutically acceptable salt thereof.

Another embodiment of the invention is a compound of formula (I), as set forth above in the Summary of the Invention, having the following formula (Ib):

(Ib)

wherein:
$R^2$ is selected from the group consisting of hydrogen, cycloalkyl and —$C(O)$—$R^5$—$N(R^3)R^4$; and
each $R^3$ and $R^4$ is independently selected from the group consisting of hydrogen and alkyl;
as an isolated stereoisomer or a mixture thereof, or as a pharmaceutically acceptable salt thereof.

Another embodiment of the invention is a compound of formula (Ib), as set forth above, which is selected from the group consisting of:
1-(1,4-ethano-8-phenyl-1,2,3,4-tetrahydro-1,5-naphthyridin-6-yl)-$N^3$-(5,6,7,8-tetrahydro-1,6-naphthyridine-3-yl)-1H-1,2,4-triazole-3,5-diamine;
1-(1,4-ethano-8-phenyl-1,2,3,4-tetrahydro-1,5-naphthyridin-6-yl)-$N^3$-(6-[((dimethyl)amino)methylcarbonyl]-5,6,7,8-tetrahydro-1,6-naphthyridine-3-yl)-1H-1,2,4-triazole-3,5-diamine; and
1-(1,4-ethano-8-phenyl-1,2,3,4-tetrahydro-1,5-naphthyridin-6-yl)-$N^3$-(6-(cyclopentyl)-5,6,7,8-tetrahydro-1,6-naphthyridine-3-yl)-1H-1,2,4-triazole-3,5-diamine,
as an isolated stereoisomer or a mixture thereof, or as a pharmaceutically acceptable salt thereof.

Another embodiment of the invention is a compound of formula (II), as set forth above in the Summary of the Invention, as an isolated stereoisomer or a mixture thereof, or as a pharmaceutically acceptable salt thereof.

Another embodiment of the invention is a compound of formula (II), as set forth above in the Summary of the Invention, which is selected from the group consisting of:

1-(6,9-ethano-4-phenyl-6,7,8,9-tetrahydro-5H-pyrido[3,2-c]azepin-2-yl)-N³-(4-(4-(pyrrolidin-1-yl)piperidinyl)-3-fluorophenyl)-1H-1,2,4-triazole-3,5-diamine;

1-(1,4-ethano-8-(4-fluorophenyl)-1,2,3,4-tetrahydro-1,5-naphthyridin-6-yl)-N³-(4-(4-(pyrrolidin-1-yl)piperidinyl)-3-fluorophenyl)-1H-1,2,4-triazole-3,5-diamine;

1-(1,4-ethano-8-(3-fluorophenyl)-1,2,3,4-tetrahydro-1,5-naphthyridin-6-yl)-N³-(4-(4-(pyrrolidin-1-yl)piperidinyl)-3-fluorophenyl)-1H-1,2,4-triazole-3,5-diamine;

1-(1,4-ethano-8-(3-trifluoromethylphenyl)-1,2,3,4-tetrahydro-1,5-naphthyridin-6-yl)-N³-(4-(4-(pyrrolidin-1-yl)piperidinyl)-3-fluorophenyl)-1H-1,2,4-triazole-3,5-diamine;

1-(1,4-ethano-8-(3-methoxyphenyl)-1,2,3,4-tetrahydro-1,5-naphthyridin-6-yl)-N³-(4-(4-(pyrrolidin-1-yl)piperidinyl)-3-fluorophenyl)-1H-1,2,4-triazole-3,5-diamine; and 1-(1,4-ethano-8-(2-methylphenyl)-1,2,3,4-tetrahydro-1,5-naphthyridin-6-yl)-N³-(4-(4-(pyrrolidin-1-yl)piperidinyl)-3-fluorophenyl)-1H-1,2,4-triazole-3,5-diamine, as an isolated stereoisomer or a mixture thereof, or as a pharmaceutically acceptable salt thereof.

Another embodiment of the invention is a compound of formula (III), as set forth above in the Summary of the Invention, as an isolated stereoisomer or a mixture thereof, or as a pharmaceutically acceptable salt thereof.

Another embodiment of the invention is a compound of formula (III), as set forth above in the Summary of the Invention, which is selected from the group consisting of:

(7S)-1-(1,4-ethano-8-phenyl-1,2,3,4-tetrahydro-1,5-naphthyridin-6-yl)-N³-(7-(t-butoxycarbonylamino)-6,7,8,9-tetrahydro-5H-benzo[7]annulene-2-yl)-1H-1,2,4-triazole-3,5-diamine;

(7S)-1-(1,4-ethano-8-phenyl-1,2,3,4-tetrahydro-1,5-naphthyridin-6-yl)-N³-(7-(diethylamino)-6,7,8,9-tetrahydro-5H-benzo[7]annulene-2-yl)-1H-1,2,4-triazole-3,5-diamine;

(7S)-1-(1,4-ethano-8-phenyl-1,2,3,4-tetrahydro-1,5-naphthyridin-6-yl)-N³-(7-(dimethylamino)-6,7,8,9-tetrahydro-5H-benzo[7]annulene-2-yl)-1H-1,2,4-triazole-3,5-diamine;

(7S)-1-(1,4-ethano-8-phenyl-1,2,3,4-tetrahydro-1,5-naphthyridin-6-yl)-N³-(7-(isopropylamino)-6,7,8,9-tetrahydro-5H-benzo[7]annulene-2-yl)-1H-1,2,4-triazole-3,5-diamine;

(7S)-1-(1,4-ethano-8-phenyl-1,2,3,4-tetrahydro-1,5-naphthyridin-6-yl)-N³-(7-(cyclobutylamino)-6,7,8,9-tetrahydro-5H-benzo[7]annulene-2-yl)-1H-1,2,4-triazole-3,5-diamine;

(7S)-1-(1,4-ethano-8-phenyl-1,2,3,4-tetrahydro-1,5-naphthyridin-6-yl)-N³-(7-(dipropylamino)-6,7,8,9-tetrahydro-5H-benzo[7]annulene-2-yl)-1H-1,2,4-triazole-3,5-diamine;

(7S)-1-(1,4-ethano-8-phenyl-1,2,3,4-tetrahydro-1,5-naphthyridin-6-yl)-N³-(7-(isobutylamino)-6,7,8,9-tetrahydro-5H-benzo[7]annulene-2-yl)-1H-1,2,4-triazole-3,5-diamine; and (7S)-1-(1,4-ethano-8-phenyl-1,2,3,4-tetrahydro-1,5-naphthyridin-6-yl)-N³-(7-(diisobutylamino)-6,7,8,9-tetrahydro-5H-benzo[7]annulene-2-yl)-1H-1,2,4-triazole-3,5-diamine, as an isolated stereoisomer or a mixture thereof, or as a pharmaceutically acceptable salt thereof.

Another embodiment of the invention is a compound of formula (IV), as set forth above in the Summary of the Invention, as an isolated stereoisomer or a mixture thereof, or as a pharmaceutically acceptable salt thereof.

Another embodiment of the invention is a compound of formula (IV), as set forth above in the Summary of the Invention, which is a compound of the following formula (IVa):

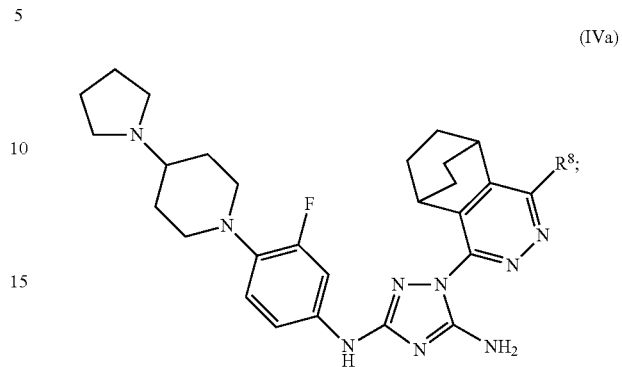

(IVa)

wherein:

R⁸ is selected from the group consisting of halo, pyridinyl, benzodioxolyl and phenyl optionally substituted by a substituent selected from the group consisting of cyano and alkyl;

as an isolated stereoisomer or a mixture thereof, or as a pharmaceutically acceptable salt thereof.

Another embodiment of the invention is a compound of formula (IVa), as set forth above, which is selected from the group consisting of:

1-(4-chloro-5,8-ethano-5,6,7,8-tetrahydrophthalazine-1-yl)-N³-(4-(4-(pyrrolidin-1-yl)piperidinyl)-3-fluorophenyl)-1H-1,2,4-triazole-3,5-diamine;

1-(4-(2-chlorophenyl)-5,8-ethano-5,6,7,8-tetrahydrophthalazine-1-yl)-N³-(4-(4-(pyrrolidin-1-yl)piperidinyl)-3-fluorophenyl)-1H-1,2,4-triazole-3,5-diamine;

1-(4-(3-cyanophenyl)-5,8-ethano-5,6,7,8-tetrahydrophthalazine-1-yl)-N³-(4-(4-(pyrrolidin-1-yl)piperidinyl)-3-fluorophenyl)-1H-1,2,4-triazole-3,5-diamine;

1-(4-(benzo[d][1,3]dioxol-5-yl)-5,8-ethano-5,6,7,8-tetrahydrophthalazine-1-yl)-N³-(4-(4-(pyrrolidin-1-yl)piperidinyl)-3-fluorophenyl)-1H-1,2,4-triazole-3,5-diamine;

1-(4-(pyridin-4-yl)-5,8-ethano-5,6,7,8-tetrahydrophthalazine-1-yl)-N³-(4-(4-(pyrrolidin-1-yl)piperidinyl)-3-fluorophenyl)-1H-1,2,4-triazole-3,5-diamine; and 1-(4-(3-methylphenyl)-5,8-ethano-5,6,7,8-tetrahydrophthalazine-1-yl)-N³-(4-(4-(pyrrolidin-1-yl)piperidinyl)-3-fluorophenyl)-1H-1,2,4-triazole-3,5-diamine, as an isolated stereoisomer or a mixture thereof, or as a pharmaceutically acceptable salt thereof.

Another embodiment of the invention is a compound of formula (IV), as set forth above in the Summary of the Invention, which is a compound of the following formula (IVb):

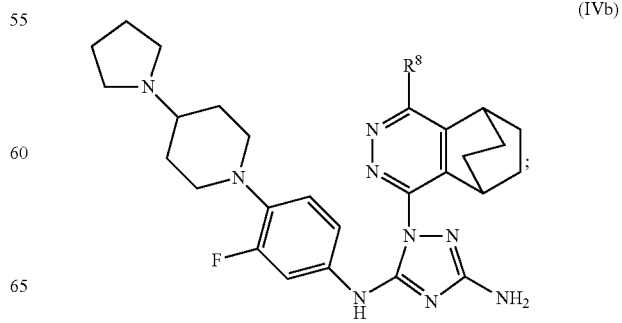

(IVb)

wherein:

R⁸ is selected from the group consisting of halo, pyridinyl, benzodioxolyl and phenyl optionally substituted by a substituent selected from the group consisting of cyano and alkyl;

as an isolated stereoisomer or a mixture thereof, or as a pharmaceutically acceptable salt thereof.

Another embodiment of the invention is a compound of formula (IVb), as set forth above, which is 1-(4-chloro-5,8-ethano-5,6,7,8-tetrahydrophthalazine-1-yl)-$N^5$-(4-(4-(pyrrolidin-1-yl)piperidinyl)-3-fluorophenyl)-1H-1,2,4-triazole-3,5-diamine, as an isolated stereoisomer or a mixture thereof, or as a pharmaceutically acceptable salt thereof.

Another embodiment of the invention is a compound of formula (V), as set forth above in the Summary of the Invention, as an isolated stereoisomer or a mixture thereof, or as a pharmaceutically acceptable salt thereof.

Another embodiment of the invention is a compound of formula (V), as set forth above in the Summary of the Invention, which is selected from the group consisting of:

(3S)-1-(4-chloro-5,8-ethano-5,6,7,8-tetrahydrophthalazine-1-yl)-$N^3$-(6-(4-(cyclopropylmethyl)-3-methylpiperazin-1-yl)pyridin-3-yl)-1H-1,2,4-triazole-3,5-diamine;

(3S)-1-(4-phenyl-5,8-ethano-5,6,7,8-tetrahydrophthalazine-1-yl)-$N^3$-(6-(4-(cyclopropylmethyl)-3-methylpiperazin-1-yl)pyridin-3-yl)-1H-1,2,4-triazole-3,5-diamine;

(3S)-1-(4-(2-chlorophenyl)-5,8-ethano-5,6,7,8-tetrahydrophthalazine-1-yl)-$N^3$-(6-(4-(cyclopropylmethyl)-3-methylpiperazin-1-yl)pyridin-3-yl)-1H-1,2,4-triazole-3,5-diamine;

(3S)-1-(4-(3-methylphenyl)-5,8-ethano-5,6,7,8-tetrahydrophthalazine-1-yl)-$N^3$-(6-(4-(cyclopropylmethyl)-3-methylpiperazin-1-yl)pyridin-3-yl)-1H-1,2,4-triazole-3,5-diamine; and (3S)-1-(4-(pyridin-4-yl)-5,8-ethano-5,6,7,8-tetrahydrophthalazine-1-yl)-$N^3$-(6-(4-(cyclopropylmethyl)-3-methylpiperazin-1-yl)pyridin-3-yl)-1H-1,2,4-triazole-3,5-diamine, as an isolated stereoisomer or a mixture thereof, or as a pharmaceutically acceptable salt thereof.

Another embodiment of the invention is a compound of formula (VI), as set forth above in the Summary of the Invention, as an isolated stereoisomer or a mixture thereof, or as a pharmaceutically acceptable salt thereof.

Another embodiment of the invention is a compound of formula (VI), as set forth above in the Summary of the Invention, which is selected from the group consisting of:

1-(4-chloro-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine;

1-(4-phenyl-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine;

1-(4-(2-chlorophenyl)-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine;

1-(4-(3-methylphenyl)-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine;

1-(4-(3-cyanophenyl)-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine;

1-(4-(2-ethoxy-5-methylphenyl)-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine;

1-(4-(4-fluoro-2-methylphenyl)-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine; and 1-(4-(pyridin-4-yl)-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine, as an isolated stereoisomer or a mixture thereof, or as a pharmaceutically acceptable salt thereof.

Another embodiment of the invention is a compound of formula (VII), as set forth above in the Summary of the Invention, as an isolated stereoisomer or a mixture thereof, or as a pharmaceutically acceptable salt thereof.

Another embodiment of the invention is a compound of formula (VII), as set forth above in the Summary of the Invention, which is selected from the group consisting of:

1-(4-phenyl-5,6,7,8-tetrahydroquinazoline-2-yl)-$N^3$-(4-(4-(pyrrolidin-1-yl)piperidinyl)-3-fluorophenyl)-1H-1,2,4-triazole-3,5-diamine; and 1-(5,8-ethano-4-phenyl-5,6,7,8-tetrahydropyrido[3,2-d]pyrimidin-2-yl)-$N^3$-(4-(4-(pyrrolidin-1-yl)piperidinyl)-3-fluorophenyl)-1H-1,2,4-triazole-3,5-diamine, as an isolated stereoisomer or a mixture thereof, or as a pharmaceutically acceptable salt thereof.

Of the various aspects of the pharmaceutical compositions of the invention comprising a pharmaceutically acceptable excipient and a therapeutically effective amount of a compound of the invention, as set forth above in the Summary of the Invention, certain embodiments are preferred.

Of the various aspects of methods of treating a disease or condition associated with Axl activity in a mammal, wherein the method comprises administering to a mammal in need thereof a therapeutically effective amount of a compound of the invention, as set forth above in the Summary of the Invention, certain embodiments are preferred.

One embodiment of these methods is the method wherein the disease or condition is selected from the group consisting of rheumatoid arthritis, vascular disease, vascular injury, psoriasis, visual impairment due to macular degeneration, diabetic retinopathy, retinopathy of prematurity, kidney disease, osteoporosis, osteoarthritis and cataracts.

One embodiment of these methods is the method wherein a manifestation of the disease or condition is solid tumor formation in said mammal.

One embodiment of these methods is the method wherein the disease or condition is selected from the group consisting of breast carcinoma, renal carcinoma, endometrial carcinoma, ovarian carcinoma, thyroid carcinoma, non-small cell lung carcinoma, and uveal melanoma.

One embodiment of these methods is the method wherein a manifestation of the disease or condition is liquid tumor formation in said mammal.

One embodiment of these methods is the method wherein the disease or condition is myeloid leukemia or lymphoma.

One embodiment of these methods is the method wherein the disease or condition is endometriosis.

One embodiment of these methods is the method wherein the disease or condition is metastasis to the liver.

Another embodiment of the invention are those methods of treating a disease or condition associated with Axl activity by administering to the mammal a therapeutically effective amount of a pharmaceutical composition of the invention, as set forth above in the Summary of the Invention, wherein the disease or condition is selected from the group consisting of rheumatoid arthritis, vascular disease/injury (including but not limited to restenosis, atherosclerosis and thrombosis), psoriasis, visual impairment due to macular degeneration, diabetic retinopathy or retinopathy of prematurity, kidney disease (including but not limited to glomerulonephritis, diabetic nephropathy and renal transplant rejection), osteoporosis, osteoarthritis and cataracts.

Another embodiment of the invention are those methods of treating a disease or condition associated with Axl activity by administering to the mammal a therapeutically effective amount of a pharmaceutical composition of the invention, as set forth above in the Summary of the Invention, wherein the disease or condition is selected from the group consisting of breast carcinoma, renal carcinoma, endometrial carcinoma, ovarian carcinoma, thyroid carcinoma, non-small cell lung carcinoma, melanoma, prostate carcinoma, sarcoma, gastric cancer, uveal melanoma, myeloid leukemia and lymphoma.

Another embodiment of the invention are those methods of treating a disease or condition associated with Axl activity by administering to the mammal of therapeutically effective amount of a pharmaceutical composition of the invention, as set forth above in the Summary of the Invention, wherein the disease or condition is endometriosis.

Specific embodiments of the invention are described in more detail in the following sections.

Utility and Testing of the Compounds of the Invention

The oncogenic RTK, Axl, was recently identified, using a retroviral-based functional genetic screening protocol, as a regulator of haptotactic migration, which is a key event in angiogenesis. Axl inhibition by RNAi-mediated silencing blocked endothelial cell migration, proliferation and in vitro tube formation. These observations, which were disclosed at the American Association Cancer Research General Meeting, Apr. 16-20, 2005, Anaheim, Calif., and The 7th Annual Symposium on Anti-Angiogenic Agents, Feb. 10-13, 2005, San Diego, Calif.; (*Requirement for The Receptor Tyrosine Kinase Axl in Angiogenesis and Tumor Growth*, Holland, S. J. Powell, M. J., Franci, C., Chan, E., Friera, A. M., Atchison, R., Xu, W., McLaughlin, J., Swift, S. E., Pali, E., Yam, G., Wong, S., Xu, X., Hu, Y., Lasaga, J., Shen, M., Yu, S., Daniel, R., Hitoshi, Y., Bogenberger, J., Nor, J. E., Payan, D. G and Lorens, J. B), were substantiated by an in vivo study which demonstrated that stable, shRNAi-mediated Axl knockdown impaired formation of functional human blood vessels in a mouse model of human angiogenesis. These observations were published in a peer reviewed journal (Holland S J, Powell M J, Franci C, Chan E W, Friera A M, Atchison R E, McLaughlin J, Swift S E, Pali E S, Yam G, Wong S, Lasaga J, Shen M R, Yu S, Xu W, Hitoshi Y, Bogenberger J, Nor J E, Payan D G, Lorens J B. "Multiple roles for the receptor tyrosine kinase axl in tumor formation." *Cancer Res*. (2005) Vol 65 pp 9294-303. These observations are also disclosed in U.S. Published Patent Application 2005/0118604 and European Patent Application 1 563 094, the disclosures of which are incorporated in full by reference. Axl signaling, therefore, impacts multiple functions required for neovascularization in vitro, and regulates angiogenesis in vivo. Regulation of these pro-angiogenic processes required the catalytic activity of Axl. Thus, Axl-mediated angiogenic stimulation would be amenable to modulation by a small molecule inhibitor of Axl catalytic activity.

Accordingly, the compounds of the invention are small molecule inhibitors of Axl catalytic activity, and are therefore useful in treating diseases and conditions which are associated with Axl catalytic activity including those diseases and conditions which are characterized by angiogenesis and/or cell proliferation. In particular, the compounds of the invention and pharmaceutical compositions of the invention are useful in treating diseases and conditions which are alleviated by the modulation of Axl activity. For purposes of this invention, diseases and conditions which are alleviated by the "modulation of Axl activity" includes diseases and conditions which are alleviated by a decrease in Axl activity and diseases and conditions which are alleviated by an increase in Axl activity. Preferably such diseases and conditions are alleviated by a decrease in Axl activity. Diseases and conditions which are alleviated by the modulation of Axl activity include, but are not limited to, solid tumors, including, but not limited to, breast, renal, endometrial, ovarian, thyroid, and non-small cell lung carcinoma, melanoma, prostate carcinoma, sarcoma, gastric cancer and uveal melanoma; liquid tumors, including but not limited to, leukemias (particularly myeloid leukemias) and lymphomas; endometriosis, vascular disease/injury (including but not limited to restenosis, atherosclerosis and thrombosis), psoriasis; visual impairment due to macular degeneration; diabetic retinopathy and retinopathy of prematurity; kidney disease (including but not limited to glomerulonephritis, diabetic nephropathy and renal transplant rejection), rheumatoid arthritis; osteoarthritis, osteoporosis and cataracts.

In addition to the foregoing, the compounds of the invention are useful in treating diseases and conditions which are affected by the following biological processes: Invasion, migration, metastasis, or drug resistance as manifested in cancer; stem cell biology as manifested in cancer; invasion, migration, adhesion, or angiogenesis as manifested in endometriosis; vascular remodeling as manifested in cardiovascular disease, hypertension or vascular injury; bone homeostasis as manifested in osteoporosis or osteoarthritis; viral infection as manifested, for example, in ebola virus infection; or differentiation as manifested in obesity. The compounds of the invention may also be used to modulate inflammatory processes by treating sepsis, acting as vaccine adjuvants, and/or potentiating the immune response in immuno-compromised patients.

In one embodiment, the compounds of the invention are effective in treating metastasis to the liver. For example, treatment with compounds of the invention can result in pronounced reduction in the development of liver micrometastases. One method of the invention is treatment of a patient with compounds of the invention to reduce metastasis to the liver. This method can be done with compounds of the invention alone or in combination with other agents to produce therapeutic benefit.

The compounds of the invention are also useful in treating cell proliferative disorders. A cell proliferative disorder refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

Generally, cell proliferative disorders treatable with the compounds of the invention relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, ovarian cancer, renal cancer, gastrointestinal cancer, kidney cancer, bladder cancer, pancreatic cancer, lung squamous carcinoma, and adenocarcinoma.

Therefore, in addition to the foregoing, the compounds of the invention are useful in treating renal cell carcinoma, clear cell carcinoma of kidney, and renal cell adenocarcinoma; invasive ductal carcinoma, invasive lobular carcinoma, ductal carcinoma, lobular carcinoma in situ, and metastatic breast cancer; basal cell carcinoma, squamous cell carcinoma, malignant melanoma, and Karposi's sarcoma; small cell and non-small cell lung carcinoma, bronchial adema, pleuropulmonary blastoma, and malignant mesothelioma; brain stem and hyptothalamic glioma, cerebellar and cerebral astrocytoma, medullablastoma, ependymal tumors, oligodendroglial, meningiomas, and neuroectodermal and pineal tumors; prostate cancer, testicular cancer, and penile cancer; uterine cancer (endometrial), cervical, ovarian, vaginal, vulval cancers, uterine sarcoma, ovarian germ cell tumor; anal, colon, colorectal, esophageal, gallbladder, stomach (gastric), pancreatic cancer, pancreatic cancer-Islet cell, rectal, small-intestine, and salivary gland cancers; hepatocellular carcinoma, cholangiocarcinoma, mixed hepatocellular cholangiocarcinoma, and primary liver cancer; intraocular melanoma, retinoblastoma, and rhabdomyosarcoma; laryngeal, hypopharyngeal, nasopharyngeal, oropharyngeal cancers, and lip and oral cancer; squamous neck cancer; metastatic paranasal sinus cancer; B cell and C cell lymphomas, non-Hodgkins lymphoma, cutaneous T cell lymphoma, Hodgkins disease, and lymphoma of the central nervous system; acute myelogenous (myeloid) leukemia, acute lymphoblastic leukemia, chronic lymphocytic leukemia, chronic myelogenous leukemia, and hairy cell leukemia; thyroid cancer, thymoma, and malignant thymoma; bladder cancer; and sarcoma of the soft tissue, osteosarcoma, malignant fibrous histiocytoma, lymphosarcoma, and rhabdomyosarcoma.

Of the B cell lymphoma group of diseases and conditions, the compounds of the invention are useful in treating precursor B-lymphoblastic leukemia/lymphoma (precursor B-cell acute lymphoblastic leukemia), B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia Of the T cell lymphoma group of diseases and conditions, the compounds of the invention are useful in treating precursor T-lymphoblastic lymphoma/leukemia (precursor T-cell acute lymphoblastic leukemia), T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, mycosis fungoides/Sezary syndrome, anaplastic large-cell lymphoma, T/null cell, primary cutaneous type, peripheral T-cell lymphoma not otherwise characterized, angioimmunoblastic T-cell lymphoma, anaplastic large-cell lymphoma, T/null cell, primary systemic type.

Of the Hodgkins disease group, the compounds of the invention are useful in treating nodular lymphocyte-predominant Hodgkin's lymphoma, nodular sclerosis Hodgkin's lymphoma (grades 1 and 2), lymphocyte-rich classical Hodgkin's lymphoma, mixed cellularity Hodgkin's lymphoma, and lymphocyte depletion Hodgkin's lymphoma.

The compounds of the invention are also useful in treating myelogenous leukemia (e.g., Philadelphia chromosome positive (t(9;22)(qq34;q11)), chronic neutrophilic leukemia, chronic eosinophilic leukemia/hypereosinophilic syndrome, chronic idiopathic myelofibrosis, polycythemia vera, and essential thrombocythemia, chronic myelomonocytic leukemia, atypical chronic myelogenous leukemia, and juvenile myelomonocytic leukemia, refractory anemia (with ringed sideroblasts and without ringed sideroblasts), refractory cytopenia (myelodysplastic syndrome) with multilineage dysplasia, refractory anemia (myelodysplastic syndrome) with excess blasts, 5q-syndrome, and myelodysplastic syndrome with t(9;12)(q22;p12).

The compounds of the invention are also useful in treating acute myelogenous leukemia with t(8;21)(q22;q22), AML1 (CBF-alpha)/ETO, acute promyelocytic leukemia (AML with t(15;17)(q22;q11-12) and variants, PML/RAR-alpha), acute myelogenous leukemia with abnormal bone marrow eosinophils (inv(16)(p13q22) or t(16;16)(p13;q11), CBFb/MYH11X), and acute myelogenous leukemia with 11q23 (MLL) abnormalities, acute myelogenous leukemia minimally differentiated, acute myelogenous leukemia without maturation, acute myelogenous leukemia with maturation, acute myelomonocytic leukemia, acute monocytic leukemia, acute erythroid leukemia, acute megakaryocytic leukemia, acute basophilic leukemia, and acute panmyelosis with myelofibrosis.

The following animal models provide guidance to one of ordinary skill in the art in testing the compounds of the invention for their use in treating the disease or condition indicated.

The compounds of the invention may be tested for their use in treating leukemias and lymphomas by testing the compounds in the xenograft in SCID mouse model using human Axl-expressing cancer cell lines including, but not limited to, HeLa, MDA-MB-231, SK-OV-3, OVCAR-8, DU145, H1299, ACHN, A498 and Caki-1.

The compounds of the invention may be tested for their use in treating leukemias in the xenograft in SCID or nu/nu mouse model using human Axl-expressing AML and CML leukemia cell lines.

The compounds of the invention may be tested for their use in treating endometriosis by using the syngenic mouse model of endometriosis (see Somigliana, E. et al., "Endometrial ability to implant in ectopic sites can be prevented by interleukin-12 in a murine model of endometriosis", *Hum. Reprod.* (1999), Vol. 14, NO. 12, pp. 2944-50). The compounds may also be tested for their use in treating endometriosis by using the rat model of endometriosis (see Lebovic, D. I. et al., "Peroxisome proliferator-activated receptor-gamma induces regression of endometrial explants in a rat model of endometriosis", *Fertil. Steril.* (2004), 82 Suppl 3, pp. 1008-13).

The compounds of the invention may be tested for their use in treating restenosis by using the balloon-injured rate carotid artery model (see Kim, D. W. et al., "Novel oral formulation of paclitaxel inhibits neointimal hyperplasia in a rat carotid artery injury model", *Circulation* (2004), Vol. 109, No. 12, pp. 1558-63, Epub 2004 Mar. 8).

The compounds of the invention may also be tested for their use in treating restenosis by using the percutaneous transluminal coronary angioplasty in apoE deficient mouse model (see von der Thusen, J. H. et al., "Adenoviral transfer of endothelial nitric oxide synthase attenuates lesion formation in a novel murine model of postangioplasty restenosis", *Arterioscler. Thromb. Vasc. Biol.* (2004), Vol. 24, No. 2, pp. 357-62).

The compounds of the invention may be tested for their use in treating atherosclerosis/thrombosis in the ApoE deficient mouse model (see Nakashima, Y. et al., "ApoE-deficient mice develop lesions of all phases of atherosclerosis throughout the arterial tree", *Arterioscler. Thromb.* (1994), Vol. 14, No. 1, pp. 133-40).

The compounds of the invention may also be tested for their use in treating thrombosis using the collagen-epinephrin-induced pulmonary thromboembolism model and the stasis induced venous thrombosis model (see Angelillo-Scherrer A. et al., "Role of Gas6 receptors in platelet signaling during thrombus stabilization and implications for antithrombotic therapy", *J Clin Invest.* (2005) Vol 115 pp 237-46).

The compounds of the invention may be tested for their use in treating psoriasis by using the SCID mouse model or the human skin model of psoriasis (see Nickoloff, B. J. et al., "Severe combined immunodeficiency mouse and human psoriatic skin chimeras. Validation of a new animal model", *Am. J. Pathol.* (1995), Vol. 146, No. 3, pp. 580-8).

The compounds of the invention may be tested for their use in treating age-related macular degeneration or diabetic retinopathy by using the rat corneal angiogenesis model (see Sarayba M A, Li L, Tungsiripat T, Liu N H, Sweet P M, Patel A J, Osann K E, Chittiboyina A, Benson S C, Pershadsingh H A, Chuck R S. Inhibition of corneal neovascularization by a peroxisome proliferator-activated receptor-gamma ligand. *Exp Eye Res*. 2005 March; 80(3):435-42) or the laser-induced mouse choroidal neovasculation model (see Bora, P. S., et al., "Immunotherapy for choroidal neovascularization in a laser-induced mouse model simulating exudative (wet) macular degeneration", *Proc. Natl. Acad. Sci. U.S.A*. (2003), Vol. 100, No. 5, pp. 2679-84, Epub 2003 Feb. 14).

The compounds of the invention may be tested for their use in treating retinopathy of prematurity in the mouse retinopathy of prematurity model (see Smith, L. E. et al., "Oxygen-induced retinopathy in the mouse", *Invest. Ophthalmol. Vis. Sci.* (1994), Vol. 35, No. 1, pp. 101-11).

The compounds of the invention may be tested for their use in treating glomerulonephritis or diabetic nephropathy in the rat anti-Thy1.1-induced experimental mesengial proliferative glomerulonephritis model (see Smith, L. E. et al. cited above).

The compounds of the invention may be tested for their use in treating renal transplant rejection by using a rat model of chronic renal transplant rejection (see Yin, J. L. et al., "Expression of growth arrest-specific gene 6 and its receptors in a rat model of chronic renal transplant rejection", *Transplantation* (2002), Vol. 73, No. 4, pp. 657-60).

The compounds of the invention may be tested for their use in treating rheumatoid arthritis by using the CAIA mouse model (see Phadke, K. et al., "Evaluation of the effects of various anti-arthritic drugs on type II collagen-induced mouse arthritis model", *Immunopharmacology* (1985), Vol. 10, No. 1, pp. 51-60).

The compounds of the invention may be tested for their use in treating osteoarthritis by using the STR/ORT mouse model (see Brewster, M. et al., "Ro 32-3555, an orally active collagenase selective inhibitor, prevents structural damage in the STR/ORT mouse model of osteoarthritis", *Arthritis. Rheum*. (1998), Vol. 41, No. 9, pp. 1639-44).

The compounds of the invention may be tested for their use in treating osteoporosis by using the ovariectomized rat model (see Wronski, T. J. et al., "Endocrine and pharmacological suppressors of bone turnover protect against osteopenia in ovariectomized rats", *Endocrinology* (1989), Vol. 125, no. 2, pp 810-6) or the ovariectomized mouse model (see Alexander, J. M. et al., "Human parathyroid hormone 1-34 reverses bone loss in ovariectomized mice", *J Bone Miner Res*. (2001), Vol. 16, no. 9, pp 1665-73; Fujioka, M. et al., "Equol, a metabolite of daidzein, inhibits bone loss in ovariectomized mice", *J Nutr*. (2004), Vol. 134, no. 10, pp 2623-7).

The compounds of the invention may be tested for their use in treating cataracts by using the $H_2O_2$-induced model (see Kadoya, K. et al., "Role of calpain in hydrogen peroxide induced cataract", *Curr. Eye Res*. (1993), Vol. 12, No. 4, pp. 341-6) or the Emory mouse model (see Sheets, N. L. et al., "Cataract- and lens-specific upregulation of ARK receptor tyrosine kinase in Emory mouse cataract", *Invest. Ophthalmol. Vis. Sci*. (2002), Vol. 43, No. 6, pp. 1870-5).

Pharmaceutical Compositions of the Invention and Administration

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: *The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 75% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One of ordinary skill in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 kg mammal) from about 0.001 mg/kg (i.e., 0.07 mg) to about 100 mg/kg (i.e., 7.0 gm); preferably a therapeutically effective dose is (for a 70 kg mammal) from about 0.01 mg/kg (i.e., 0.7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

Compounds of the invention, or pharmaceutically acceptable salts thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Preparation of the Compounds of the Invention

The following Reaction Schemes illustrate methods to make compounds of this invention as described above in the Summary of the Invention, as isolated stereoisomers or mixtures thereof, as tautomers or mixtures thereof, or as pharmaceutically acceptable salts or N-oxides. It is understood that in the following Reaction Schemes, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include benzyl, t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acids include alkyl, aryl or arylalkyl esters.

Protecting groups may be added or removed in accordance with standard techniques, which are known to one of ordinary skill in the art and as described herein.

The use of protecting groups is described in detail in Greene, T. W. and P. G. M. Wuts, *Greene's Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

It is understood that one of ordinary skill in the art would be able to make the compounds of the invention by methods similar to the methods described herein or by methods known to one of ordinary skill in the art. It is also understood that one of ordinary skill in the art would be able to make in a similar manner as described below other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention. $^1$H NMR spectra were recorded in CDCl$_3$, DMSO-d$_6$, CD$_3$OD, Acetone-d$_6$ with trimethylsilane (TMS) as internal reference using Gemini 300 MHz instrument. Reagents and solvents were purchased from commercial sources and used without further purification. Flash column chromatography was conducted using silica gel (230-400 mesh) under a positive pressure of nitrogen. LCMS spectra for purity and mass were recorded using Waters LCMS instruments. Deionized water was used to dilute the reactions and wash the products. Brine used was prepared by dissolving sodium chloride into deionized water to saturation point.

The following Reaction Scheme 1 illustrates a general method of preparing the compounds of the invention wherein $R^{14}$ represents a substituent at the $N^3$ position of the central diaminotriazole moiety in the compounds of the invention and $R^{15}$ represents a substituent at the 1-position of the central diaminotriazole moiety in the compounds of the invention:

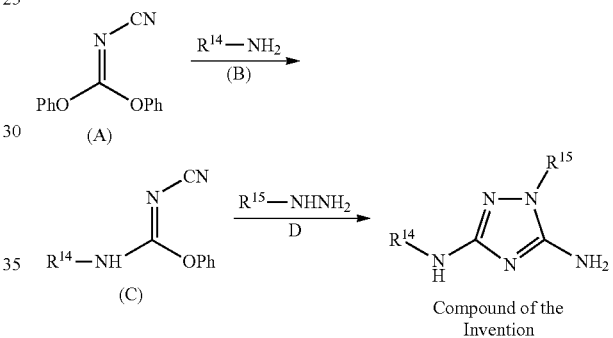

Compound of the Invention

Compounds of formula (A), formula (B) and formula (D) are commercially available or can be prepared by methods known to one skilled in the art or by methods disclosed herein.

In general, compounds of the invention are prepared, as set forth above by Reaction Scheme 1, by first treating a compound of formula (A) (where the phenyl groups therein may be replaced with other suitable groups or suitably substituted groups known to one skilled in the art) (1.1 equiv) with an equivalent amount of an aniline of formula (B) in an polar solvent, including, but not limited to, isopropyl alcohol, at ambient temperatures overnight. The diarylisourea product of formula (C) generally precipitates and isolation can be accomplished via filtration, washing with an appropriate solvent, and drying. Hydrazine hydrate of formula (D) (2 equivalents) is added to a slurry of the compound of formula (C) in an alcohol or other appropriate solvent. Generally, the ring formation reaction occurs at ambient temperature and the resulting compound of the invention can be isolated by standard isolation techniques.

Compounds of the invention wherein the $R^{15}$ substituent is attached to the nitrogen at the 2-position (instead of the 1-position as illustrated above) can be prepared using the synthetic route outlined in Reaction Scheme 1 in varying amounts depending on the steric and electronic nature of the substituents thereon as well as the particular reaction conditions employed. In some instances, compounds of the invention wherein the $R^{15}$ substituent is attached to the nitrogen at the 2-position are isolated as minor isomers along with compounds of the invention wherein the $R^{15}$ substituent is at the 1-position as major isomers, e.g., during column chromatography, as described herein.

The following Reaction Scheme 2 illustrates a specific method of preparing compounds of formula (III), as set forth above in the Summary of the Invention, where $R^7$ is as described above for compounds of formula (III) and Ph is a phenyl group:

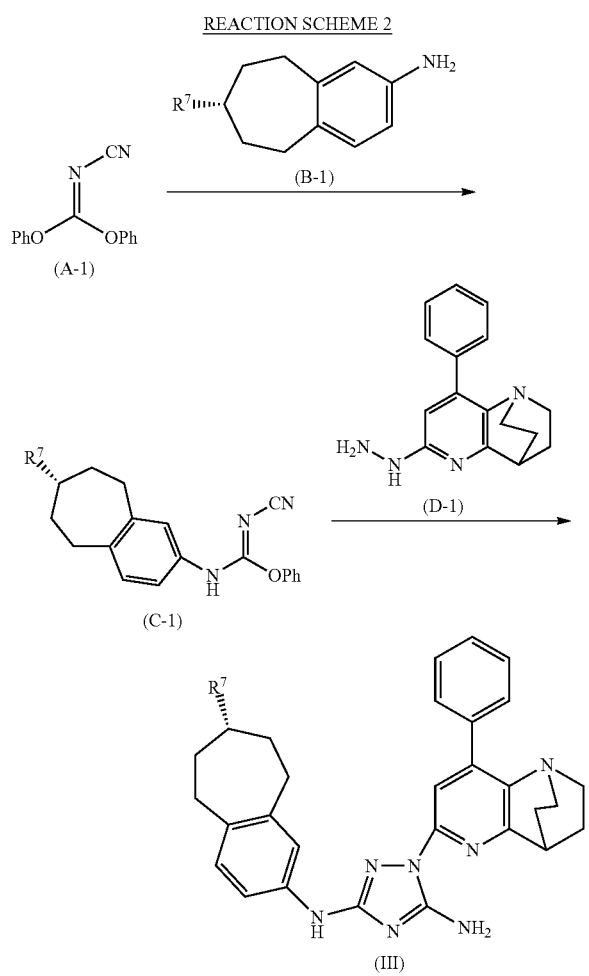

Compounds of formula (A-1), formula (B-1) and formula (D-1) are commercially available or can be prepared by methods known to one skilled in the art or by methods disclosed herein.

In general, compounds of formula (III) are prepared, as set forth by Reaction Scheme 2 above, by first treating a compound of formula (A-1) (where the phenyl groups therein may be replaced with other suitable groups or suitably substituted groups known to one skilled in the art) (1.1 equiv) with an equivalent amount of an aniline of formula (B-1) in an polar solvent, including, but not limited to, isopropyl alcohol, at ambient temperatures overnight. The diarylisourea product of formula (C-1) generally precipitates and isolation can be accomplished via filtration, washing with an appropriate solvent, and drying. Hydrazine hydrate of formula (D-1) (2 equivalents) is added to a slurry of the compound of formula (C-1) in an alcohol or other appropriate solvent. Generally, the ring formation reaction occurs at ambient temperature and the product triazole of formula (III) can be isolated by standard isolation techniques.

One of ordinary skill in the art would recognize that other compounds of the invention can be similarly prepared utilizing this method and the appropriate starting materials.

Compounds of formula (B-1) can be prepared from the corresponding ketone utilizing stereospecific transaminases. Transaminases (also known as amino transferases) are enzymes that catalyze a transamination reaction between an amino-donor molecule (such as an amine or amino acid) and an amino-acceptor molecule (such as a ketone or an α-keto acid). Specifically, enzymatic transamination involves removing the amino group from the amino-donor molecule (leaving behind a carbonyl group) and transferring the amino group to the amino-acceptor molecule (or α-keto acid) by converting the ketone moiety therein to an amine (or an amino acid). A description of transaminases and their use in stereoselective synthesis can be found in "Transminations. Enzyme Catalysis in Organic Synthesis ($2^{nd}$ Edition) (2002)", by J. David Rozzell and Andreas S. Bommarius, pp. 873-893, which is incorporated in full by reference herein.

Transaminases are particularly suitable for the enzymatic synthesis of chiral amines from the corresponding ketone precursors. Commercially available transaminases can be used to achieve a chiral enzymatic amination of a desired starting material in the preparation of the compounds of the invention. In particular, a ketone of the following formula (i) where n and m are the same and are 0, 1 or 2 and $R^{12}$ is nitro, halo or —C(O)O$R^{16}$ (where $R^{16}$ is hydrogen or alkyl) can be converted under suitable conditions to the corresponding (S)-enantiomer and (R)-enantiomer wherein the carbon to which the amino group is attached is either in the (S) or the (R) configuration, respectively, by utilizing a (S)-specific transaminase and an amino donor molecule, such as L-alanine, or a (R)-specific transaminase and an amino donor molecule, such as L-alanine, as shown below:

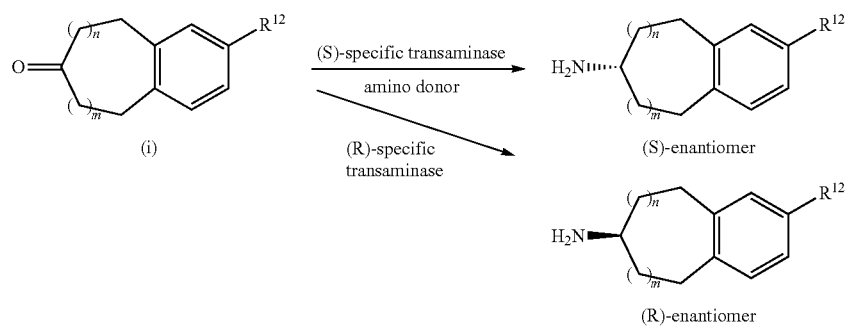

One of ordinary skill in the art would appreciate that the amino group on the (S)-enantiomer and the (R)-enantiomer can be further functionalized by standard procedures known to one skilled in the art. For example, treatment of the above (S)-enantiomer with 1,4-dibromobutane under the appropriate alkylation conditions will result in the amino group being converted to a 1-pyrrolidinyl group. Alternatively, treatment of the above (S)-enantiomer with an appropriate acylating agent with result in the amino group being acylated accordingly, and so forth.

Utilizing the appropriate transaminase to convert the cyclic ketone of formula (i) into the appropriate enantiomer, the appropriate enantiomer can be isolated in greater than 80% ee and preferably greater than 90% ee.

Compounds of formula (D-1) can be prepared according to the method disclosed below in Reaction Scheme 3:

REACTION SCHEME 3

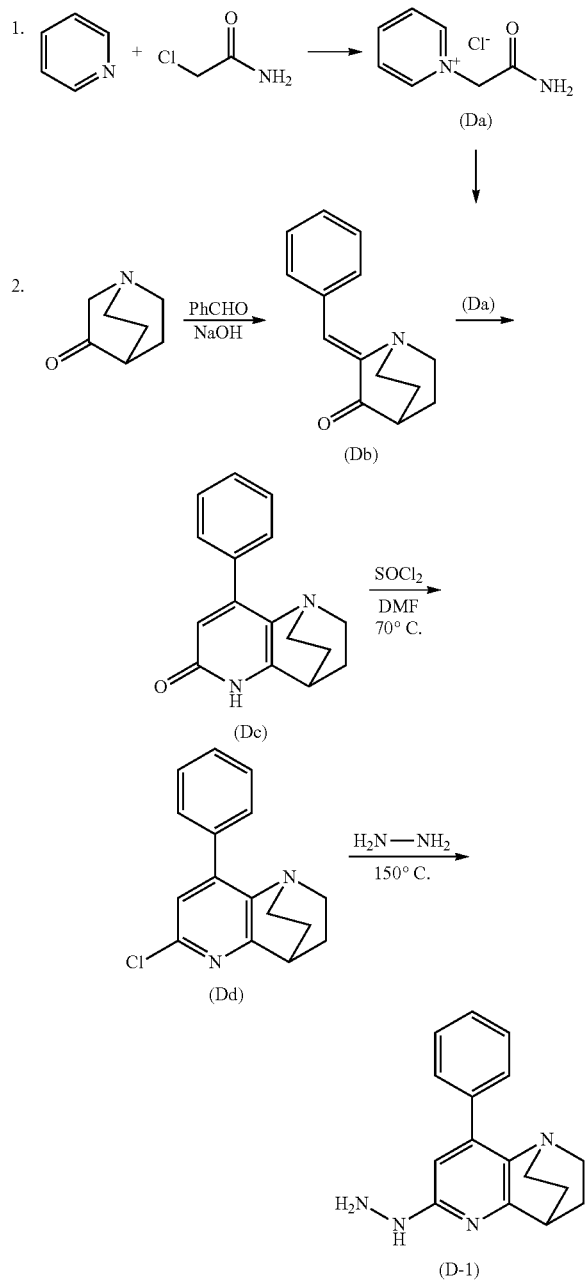

Pyridine, 2-chloroacetamide and quinuclidin-3-one are commercially available or can be prepared according to methods known to one skilled in the art.

In general, compounds of formula (D-1) are prepared, as set forth above in Reaction Scheme 3, by first treating a suspension of 2-chloroacetamide in an aprotic polar solvent, such as, but not limited to, acetonitrile, with an equimolar amount of pyridine. The reaction mixture is stirred at a suitable temperature of between about 70° C. and about 100° C. for a suitable period of time of between about 4 hours and about 10 hours. The compound of formula (Da) is isolated from the reaction mixture by standard isolation techniques, such as filtration and recrystallization.

A mixture of 3-quinuclidinone and an equimolar amount of benzaldehyde (PhCHO) in a protic solvent, such as, but not limited to, ethanol, and in the presence of a base, such as sodium hydroxide (NaOH), is refluxed for a suitable period of time of between about 1 hour and 3 hours. After the resulting solution is cooled to ambient temperature, the compound of formula (Db) is isolated by standard isolation techniques.

A solution of the compound of formula (Db) and an excess molar amount of the compound of formula (Da) in a protic solvent, such as, but not limited to, n-butanol, in the presence of a base, such as, but not limited to, pyridine, and a weak acid, such as, but not limited to, acetic acid, is stirred at a suitable temperature of between about 110° C. and about 125° C. for a suitable period of time of between about 10 hours and about 20 hours. After the reaction mixture is cooled to ambient temperature, the compound of formula (Dc) is isolated from the reaction mixture by standard isolation techniques, such as concentration, extraction and recrystallization.

To a solution of a compound of formula (Dc) in a suitable amount of thionyl chloride is added a catalytic amount of a dialkylformamide, preferably dimethylformamide (DMF). The resulting reaction mixture is heated to a suitable temperature of between about 40° C. and about 100° C., preferably of between about 60° C. and about 80° C., more preferably of between about 65° C. and about 75° C., for a suitable period of time of between about 2 hours and about 20 hours, preferably of between about 5 hours and about 15 hours, more preferably of between about 8 hours and about 12 hours. The resulting reaction mixture is allowed to cool to ambient temperature and concentrated. The resulting residue is poured over ice-water and a saturated solution of sodium carbonate is added to adjust the pH of the resulting solution to a pH of between about 10 and 11. The compound of formula (Dd) is isolated from the resulting solution by standard isolation techniques, such as concentration and purification by flash chromatography.

The compound of formula (Dd) is then treated with anhydrous ethanol and anhydrous hydrazine in the presence of an acid, such as, but not limited to, hydrochloric acid. The resulting reaction mixture is heated to a suitable temperature of between about 140° C. and about 160° C. for a suitable period of time of between about 80 hours and about 100 hours to yield the compound of formula (D-1), which is isolated from the reaction mixture by standard isolation techniques, such as concentration, extraction, removal of water and concentration.

The following Reaction 4, where the compound of formula (B-1a) is a compound of formula (i) as described above and PG represents a nitrogen protecting group such as —C(O)OR$^{13}$ where R$^{13}$ is a described above in the Summary of the Invention for compounds of formula (III), illustrates a method of preparing a compound of formula (III-2), which is a compound of formula (III) as set forth above in the Summary of the Invention, utilizing a transaminase as described above:

REACTION SCHEME 4

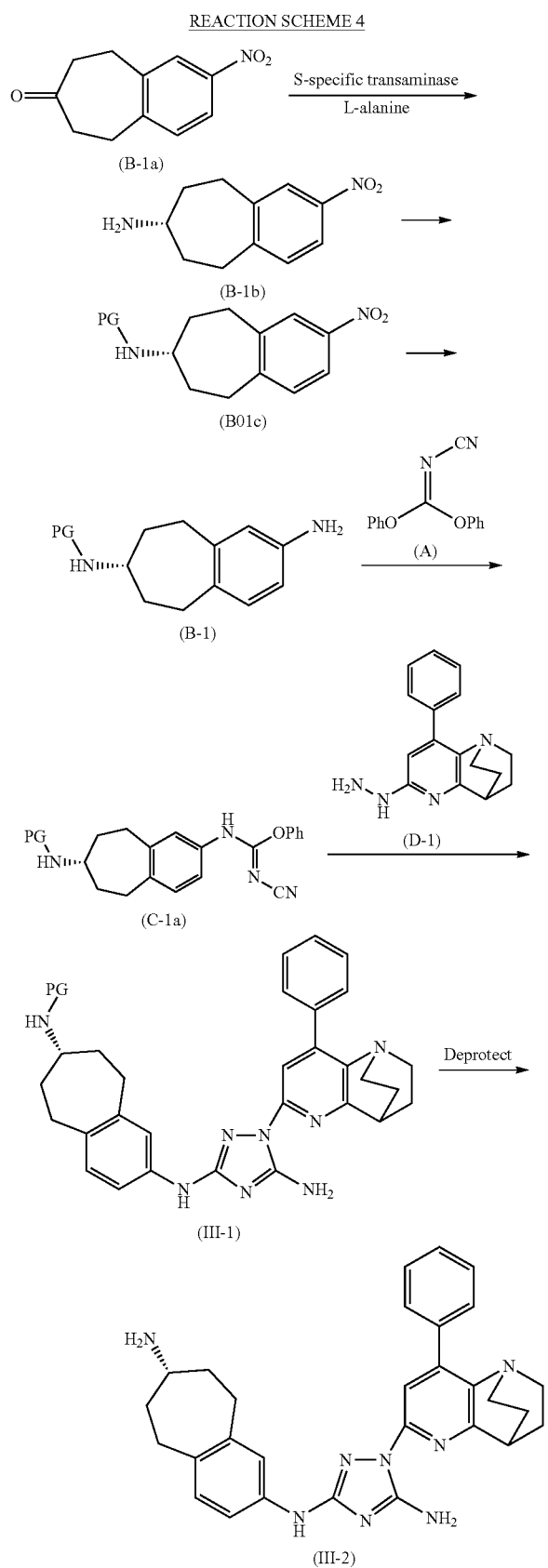

Compounds of formula (B-1a) are commercially available, or can be prepared by methods known to one skilled in the art.

Compounds of formula (D-1) can be prepared according to methods known to one skilled in the art or by methods disclosed herein. The (S)-specific transaminase is commercially available from Codexis. Preferably the (S)-specific transaminase is ATA-103 from Codexis.

In general, compounds of formula (III-1) are prepared by the method disclosed above in Reaction Scheme 4 by first converting the ketone of formula (B-1a) into the chiral compound of formula (B-1b) wherein the amino group from an amino donor molecule, preferably L-alanine, is transferred to the ketone of formula (B-1a) through an enzymatic transamination reaction under suitable conditions. In particular, the ketone of formula (B-1a) is treated with a excess molar amount of an amino donor molecule in the the presence of a catalytic amount of a transaminase, preferably a (S)-specific transaminase, and a stoichiometric or excess stoichiometric amount of a pyruvate reductase mixture that reduces (deactivates) the 2-keto acid side product, thereby driving the reaction into the desired direction. Preferably the pyruvate reductase mixture is PRM-102 from Codexix. The reaction is conducted at ambient temperature, at a pH of between about 7.5 and about 8.0, and for a period of time of between about 24 hours and about 6 days, preferably for about 4 days. The chiral compound of formula (B-1b) is isolated from the reaction mixture by standard isolation techniques known to one skilled in the art.

Alternatively, the transamination reaction can be driven to completion by coupling the reaction to a second reaction that consumes the 2-keto acid by-product in an essentially irreversible step, as described in more detail in "Transminations. Enzyme Catalysis in Organic Synthesis ($2^{nd}$ Edition) (2002)", by J. David Rozzell and Andreas S. Bommarius, pp. 873-893.

The amino group of the chiral compound of formula (B-1b) is then protected by standard nitrogen protecting procedures to yield the compound of formula (B-1c), which is isolated from the reaction mixture by standard isolation techniques known to one skilled in the art. The compound of formula (B-1c) is then treated to standard reducing conditions, such as treatment with $H_2$/Pd, to produce the corresponding aniline compound of formula (B-1), which is isolated from the reaction mixture by standard isolation techniques known to one skilled in the art. The compound of formula (B-1) is then treated with diphenyl cyanocarbonimidate of formula (A) to produce the compound of formula (C-1a), which is isolated from the reaction mixture by standard isolation techniques known to one skilled in the art.

The compound of (C-1a) is then treated with a compound of formula (D-1) in the presence of an aprotic solvent, preferably toluene, at a temperature of between about 80° C. and about 100° C. for a period of time of between about 12 hours and about 36 hours, preferably for about 24 hours, to yield a compound of formula (III-1), which is isolated from the reaction mixture by standard isolation techniques known to one skilled in the art. Compound of formula (III-1) is a compound of formula (III), as set forth above.

The protecting group on the compound of formula (III-1) can be removed under standard deprotecting conditions known to one skilled in the art, such as acid hydrolysis, to produce a compound of formula (III-2), which is isolated from the reaction mixture by standard isolation techniques known to one skilled in the art. The compound of formula (III-2) can be further treated with the appropriate aldehyde or ketone under standard reductive amination conditions to yield additional compounds of formula (III), as set forth above in the Summary of the Invention.

All compounds of the invention which exist in free base or acid form can be converted to their pharmaceutically acceptable salts by treatment with the appropriate inorganic or organic base or acid by methods known to one of ordinary skill in the art. Salts of the compounds of the invention can be converted to their free base or acid form by standard techniques known to one skilled in the art.

The following specific Synthetic Preparations (for intermediates) and Synthetic Examples (for compounds of the invention) are provided as a guide to assist in the practice of the invention, and are not intended as a limitation on the scope of the invention. The number following each compound below refers to its number in Tables 1-9, as discussed in more detail below.

SYNTHETIC PREPARATION 1

Synthesis of 1-(2-amino-2-oxoethyl)pyridinium chloride (Da)

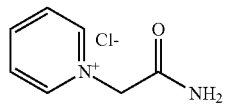

To a suspension of 2-chloroacetamide (50.00 g, 524.01 mmol) in 100 mL of acetonitrile was added pyridine (41.45 g, 524.01 mmol). After being stirred at 90° C. for 10 h, the suspension was cooled to 22° C., suction-filtered and washed with 100 mL of hexanes. The product, 1-(2-amino-2-oxoethyl)pyridinium chloride (79.10 g, yield: 87%, mp 205.2° C.), was obtained as colorless crystals after being recrystallized from methanol.

SYNTHETIC PREPARATION 2

Synthesis of (Z)-2-benzylidenequinuclidin-3-one (Db)

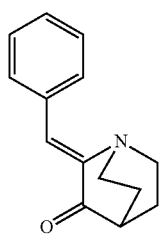 [SMILES: O=C1/C(=C/c2ccccc2)N2CCC1CC2]

A mixture of 3-quinuclidinone (20.9 g, 167 mmol), benzaldehyde (17.7 g, 167 mmol), and one pellet of sodium hydroxide in 75 mL of ethanol was refluxed for 1.5 h. After the solution was cooled, the yellow precipitates were collected, washed with ethanol, and dried to give (Z)-2-benzylidenequinuclidin-3-one (32.5 g, yield: 91.2%, mp 130-132° C.).

SYNTHETIC PREPARATION 3

Synthesis of 1,4-ethano-8-phenyl-1,2,3,4-tetrahydro-1,5-naphthyridin-6-one (Dc)

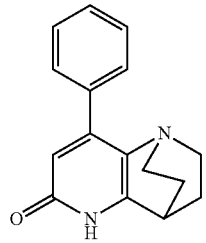 [SMILES: O=c1cc(-c2ccccc2)c2c([nH]1)C1CCN2CC1]

A solution of 2-benzylidenequiclidin-3-one (3.0 g, 14.1 mmol) and 1-(2-amino-2-oxoethyl)pyridinium chloride (7.3 g, 42.3 mmol) in butan-1-ol (100 mL) containing piperidine (5 mL) and HOAc (3 mL) was stirred at 115-120° C. for 18 h. After cooling to ambient temperature, the mixture was concentrated in vacuo and the resulting residue was partitioned between 5% MeOH in $CHCl_3$ (2×150 mL) and water. The organic phase was concentrated to give a crystalline residue, which was recrystallized from MeOH to give 1,4-ethano-8-phenyl-1,2,3,4-tetrahydro-1,5-naphthyridin-6-one (2.91 g, yield: 82%, mp 220° C.).

SYNTHETIC PREPARATION 4

Synthesis of 6-chloro-1,4-ethano-8-phenyl-1,2,3,4-tetrahydro-1,5-naphthyridine (Dd)

To a solution of 1,4-ethano-8-phenyl-1,2,3,4-tetrahydro-1,5-naphthyridin-6-one (435 mg, 1.72 mmol) in 2.5 ml of thionyl chloride was added 100 µL of DMF, and the reaction mixture was heated at 70° C. for 10 h, and concentrated in vacuo. The residue was poured on ice-water and saturated aq. $NaHCO_3$ solution was added to adjust pH to 10-11. The mixture was extracted with EtOAc (2×50 mL), dried over $Na_2SO_4$, concentrated and purified by flash chromatography (EtOAc:hexane, 1:4) to give 6-chloro-1,4-ethano-8-phenyl-1,2,3,4-tetrahydro-1,5-naphthyridine (310 mg, 66%) as a white solid; $^1H$ NMR ($CDCl_3$, 300 MHz) 7.58 (m, 2H), 7.43 (m, 3H), 7.29 (s, 1H), 3.35 (s, 1H), 3.18 (m, 2H), 2.63 (m, 2H), 1.99 (m, 2H), 1.73 (m, 2H) ppm; MS (ES) 271.39 (M+H).

SYNTHETIC PREPARATION 5

Synthesis of 6-hydrazino-1,4-ethano-8-phenyl-1,2,3,4-tetrahydro-1,5-naphthyridine (D-1) and N,N-di(tert-butoxycarbonyl)-6-hydrazino-1,4-ethano-8-phenyl-1,2,3,4-tetrahydro-1,5-naphthyridine

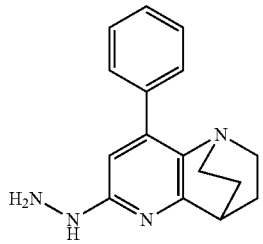 [SMILES: NNc1cc(-c2ccccc2)c2c(n1)C1CCN2CC1]

A. 6-Chloro-1,4-ethano-8-phenyl-1,2,3,4-tetrahydro-1,5-naphthyridine (1.03 g) was treated with anhydrous ethanol (10 mL), anhydrous hydrazine (Aldrich, 4.0 mL) and concentrated HCl (0.4 mL). The reaction mixture was then heated in a screw cap pressure tube at 150° C. until LCMS showed complete conversion to the hydrazine (approx. 96 h). The reaction mixture was cooled to ambient temperature, then concentrated under vacuum. The residue was partitioned between chloroform and brine. The organic layer was dried over anhydrous sodium sulfate and concentrated under vacuum to give 6-hydrazino-1,4-ethano-8-phenyl-1,2,3,4-tetrahydro-1,5-naphthyridine as a pale yellow solid (0.68 g).

B. Alternatively, in a manner similar to that described in Org. Lett. (2001), Vol. 3, No. 9, pp. 1351-1354, 6-chloro-1,4-ethano-8-phenyl-1,2,3,4-tetrahydro-1,5-naphthyridine (375 mg, 1.4 mmol), $Cs_2CO_3$ (460 mg, 1.4 mmol), di-tert-butyl-hydrazodiformate (325 mg, 1.4 mmol, Aldrich), toluene (5.0 mL), $Pd_2(dba)_3$ (90 mg, 0.1 mmol, Stern Chemicals), and DPPF (80 mg, 0.14 mmol, Stern Chemicals) were placed in a dry screw cap pressure tube charged with argon. The reaction mixture was heated at 100° C. for 48 hours until complete conversion to N,N-di(tert-butoxycarbonyl)-6-hydrazino-1,4-ethano-8-phenyl-1,2,3,4-tetrahydro-1,5-naphthyridine. Conversion was followed by TLC. After 24 hours, approximately 50% conversion occurred. Additional portions of $Cs_2CO_3$ (230 mg, 0.7 mmol), di-tert-butyl-hydrazodiformate (160 mg, 0.7 mmol, Aldrich), $Pd_2(dba)_3$ (45 mg, 0.05 mmol,), and DPPF (40 mg, 0.07 mmol) were added at this time. The reaction mixture was cooled to ambient temperature, concentrated under vacuum and purified by column chromatography on silica gel (ethyl acetate; hexane, 1:1) to give N,N-di(tert-butoxycarbonyl)-6-hydrazino-1,4-ethano-8-phenyl-1,2,3,4-tetrahydro-1,5-naphthyridine (340 mg, 52%) as a tan solid; $^1$H NMR (CDCl$_3$, 300 MHz) 7.59 (d, 2H), 7.40 (m, 3H), 7.02 (s, 1H), 3.28 (s, 1H), 3.17 (m, 2H), 2.65 (m, 2H), 1.96 (m, 2H), 1.73 (m, 2H), 1.53 (s, 9H), 1.48 (s, 9H) ppm; MS (ES) 467 (M+H).

SYNTHETIC PREPARATION 6

Synthesis of Phenyl N'-cyano-N-(7-(t-butoxycarbonylamino)-6,7,8,9-tetrahydro-5H-benzo[7]annulene-2-yl)carbamimidate (C-1a)

Finely ground 2-Nitro-8,9-dihydro-5H-benzo[7]annulen-7(6H)-one (8.00 g, 39.0 mmol) and L-alanine (34.7 g, 390 mmol) were added to the reaction buffer (1000 mL, Codexis/BioCatalytics). The mixture was stirred vigorously for about 20 min in order to obtain a uniform suspension (bright-yellow in color). The pyruvate reductase mix (40.0 g, PRM-102, Codexis/BioCatalytics) and the transaminase (0.85 g, ~10.6 wt %, ATA-103) were added. The pH of the reaction mixture was ~7. Stirring was continued at a slow pace; the pH was checked once a day and, if necessary, adjusted to pH 7.0-7.5 using 1M NaOH. During the course of the reaction the color of the mixture changed to a yellow-orange color. After 6 days, HPLC analysis showed 99% conversion. The reaction was worked up by adding sat. NaHCO$_3$ solution (200 mL) and CHCl$_3$ (600 mL). This mixture was stirred vigorously to ensure complete transfer of the product into the organic phase. After stirring overnight two layers had formed and the organic layer contained large amounts of a gel-like solid. The organic layer was separated and filtered through a large glass frit (medium) to remove the gel-like solid. The aqueous phase was extracted three times with DCM. The combined organic layers were filtered through MgSO$_4$ and the solvents were evaporated to give the desired amine, (7S)-2-nitro-7-amino-7,8,9-trihydro-5H-benzo[7]annulene (7.27 g, 91%, dark-red oil).

The single enantiomer was then BOC-protected, the nitro group reduced by treatment with H$_2$/Pd and the primary aniline treated with diphenyl cyanocarbonimidate (slight excess) in 20 mL of isopropanol with stirring at ambient temperature overnight. The solid was filtered, washed with isopropanol and ether and dried to give phenyl (7S)—N'-cyano-N-(7-amino-6,7,8,9-tetrahydro-5H-benzo[7]annulene-2-yl)carbamimidate, as a white solid in high yield (from the single enantiomer via transamination).

SYNTHETIC EXAMPLE 1

Synthesis of (7S)-1-(1,4-ethano-8-phenyl-1,2,3,4-tetrahydro-1,5-naphthyridin-6-yl)-N$^3$-(7-(t-butoxycarbonylamino)-6,7,8,9-tetrahydro-5H-benzo[7]annulene-2-yl)-1H-1,2,4-triazole-3,5-diamine Phenyl (7S)—N'-cyano-N-(7-amino-6,7,8,9-tetrahydro-5H-benzo[7]annulene-2-yl)carbamimidate (0.82 g, 1.95 mmol) and 6-hydrazino-1,4-ethano-8-phenyl-1,2,3,4-tetrahydro-1,5-naphthyridine (0.52 g, 1.95 mmol) were mixed in dry toluene (25 mL). The suspension was heated to 90° C. and stirred for 24 h. The clear solution was allowed to cool to ambient temperature and the toluene was evaporated using a rotavapor. The crude product was then checked by HPLC and TLC. Column chromatography on silica gel using CHCl$_3$/MeOH (20/1) afforded some clean fractions of product which gave 114 mg (10%) of the desired product, (7S)-1-(1,4-ethano-8-phenyl-1,2,3,4-tetrahydro-1,5-naphthyridin-6-yl)-N$^3$-(7-(t-butoxycarbonylamino)-6,7,8,9-tetrahydro-5H-benzo[7]annulene-2-yl)-1H-1,2,4-triazole-3,5-diamine, compound #25. The impure fractions were further purified by reverse phase HPLC to yield another 78 mg (7%) of the desired product; $^1$H NMR (CDCl$_3$): 8.71-9.02 (m, 3H), 7.67-7.89 (m, 1H), 7.43-7.62 (m, 5H), 7.30-7.43 (m, 1H), 7.00-7.17 (m, 2H), 4.41-4.64 (m, 1H), 3.51-3.82 (m, 4H), 2.97-3.23 (m, 2H), 2.61-2.83 (m, 5H), 2.07-2.34 (m, 4H), 1.86-2.04 (m, 2H), 1.45 (s, 9H), 1.14-1.37 (m, 2H) ppm; MS (ES) 593.29 (M+H).

SYNTHETIC EXAMPLE 2

Synthesis of (7S)-1-(1,4-ethano-8-phenyl-1,2,3,4-tetrahydro-1,5-naphthyridin-6-yl)-N$^3$-(7-(diethylamino)-6,7,8,9-tetrahydro-5H-benzo[7]annulene-2-yl)-1H-1,2,4-triazole-3,5-diamine (7S)-1-(1,4-ethano-8-phenyl-1,2,3,4-tetrahydro-1,5-naphthyridin-6-yl)-N$^3$-(7-(t-butoxycarbonylamino)-6,7,8,9- tetrahydro-5H-benzo[7]annulene-2-yl)-1H-1,2,4-triazole-3,5-diamine (23 mg, 0.038 mmol) was added to a 4M solution of HCl in dioxane. In order to improve solubility, 2 mL of MeOH were added which resulted in a clear solution. The reaction mixture was stirred for 6 h at ambient temperature and then neutralized with 2M NaOH which caused the precipitation of the free amine. The product was filtered off, washed with water and dried over night in HV to yield the amino compound, (7S)-1-(1,4-ethano-8-phenyl-1,2,3,4-tetrahydro-1,5-naphthyridin-6-yl)-$N^3$-(7-amino-6,7,8,9-tetrahydro-5H-benzo[7]annulene-2-yl)-1H-1,2,4-triazole-3,5-diamine (18 mg, 96%). The product was then dissolved in dry DCM. Subsequently, acetaldehyde (~5 mg, 0.1 mmol) and NaBH(OAc)$_3$ (21 mg, 0.1 mmol) were added. After the mixture was stirred for 2 d at ambient temperature, the solvents were evaporated and the desired product, (7S)-1-(1,4-ethano-8-phenyl-1,2,3,4-tetrahydro-1,5-naphthyridin-6-yl)-$N^3$-(7-(diethylamino)-6,7,8,9-tetrahydro-5H-benzo[7]annulene-2-yl)-1H-1,2,4-triazole-3,5-diamine, compound #35, was isolated via reverse phase HPLC (10.8 mg, 52% two steps); $^1$H NMR (DMSO-d$_6$, 300 MHz): 9.04 (s, 1H), 8.69 (s br, 1H), 7.75 (s br, 2H), 7.54-7.66 (m, 5H), 7.41 (d, 1H), 7.26 (s, 1H), 7.01 (d, 1H), 2.87-3.18 (m, 8H), 2.60-2.81 (m, 4H), 2.51-2.55 (m, 2H), 2.00-2.28 (m, 4H), 1.66-1.87 (m, 2H), 1.30-1.56 (m, 2H), 1.12-1.28 (m, 6H) ppm; MS (ES) 549.22 (M+H).

SYNTHETIC EXAMPLE 3

In a similar manner as described above utilizing the appropriately substituted starting materials and reagents, the following compounds were prepared:

1-(1,4-ethano-8-phenyl-1,2,3,4-tetrahydro-1,5-naphthyridin-6-yl)-$N^3$-(6-amino-5,6,7,8-tetrahydroquinoline-3-yl)-1H-1,2,4-triazole-3,5-diamine, compound #1, $^1$H NMR (DMSO-d$_6$, 300 MHz) 10.06 (s, 1H), 8.93 (s, 1H), 8.10 (s, 2H), 8.01 (s, 1H), 7.88 (s, 2H), 7.63 (d, 2H), 7.53 (m, 4H), 7.40 (s, 1H), 7.12 (t, 1H), 6.72 (d, 1H), 3.53 (s, 2H), 3.02 (s, 2H), 2.16 (m, 1H), 2.06 (s, 2H), 1.90 (m, 1H), 1.72 (s, 4H), 1.21 (s, 6H) ppm; MS (ES) 480.58 (M+H);

1-(1,4-ethano-8-phenyl-1,2,3,4-tetrahydro-1,5-naphthyridin-6-yl)-$N^3$-(5,6,7,8-tetrahydro-1,6-naphthyridine-3-yl)-1H-1,2,4-triazole-3,5-diamine, compound #2, $^1$H NMR (DMSO-d$_6$, 300 MHz) 9.56 (s, 1H), 9.09 (s, 2H), 8.73 (d, 1H), 7.82 (d, 3H), 7.64 (d, 2H), 7.53 (m, 4H), 4.32 (s, 2H), 3.44 (m, 3H), 3.28 (s, 2H), 2.99 (t, 2H), 2.81 (s, 2H), 2.06 (s, 2H), 1.72 (s, 2H) ppm; MS (ES) 466.20 (M+H);

1-(1,4-ethano-8-phenyl-1,2,3,4-tetrahydro-1,5-naphthyridin-6-yl)-$N^3$-(6-[(((dimethyl)amino)methyl)carbonylamino]-5,6,7,8-tetrahydroquinoline-3-yl)-1H-1,2,4-triazole-3,5-diamine, compound #3, $^1$H NMR (DMSO-d$_6$, 300 MHz) 10.11 (s, 1H), 9.68 (s, 1H), 8.96 (s, 1H), 8.66 (d, 1H), 8.00 (s, 1H), 7.87 (s, 2H), 7.63 (d, 2H), 7.57 (s, 1H), 7.51 (d, 3H), 4.16 (t, 2H), 3.87 (s, 2H), 3.51 (s, 1H), 3.15 (d, 2H), 3.03 (t, 2H), 2.79 (s, 6H), 2.73 (m, 3H), 2.05 (m, 3H), 1.88 (m, 1H), 1.70 (t, 2H) ppm; MS (ES) 565.34 (M+H);

1-(1,4-ethano-8-phenyl-1,2,3,4-tetrahydro-1,5-naphthyridin-6-yl)-$N^3$-(6-[((dimethyl)amino)methylcarbonyl]-5,6,7,8-tetrahydro-1,6-naphthyridine-3-yl)-1H-1,2,4-triazole-3,5-diamine, compound #4, $^1$H NMR (DMSO-d$_6$, 300 MHz) 9.81 (s, 1H), 9.56 (s, 1H), 8.84 (d, 1H), 8.00 (s, 1H), 7.87 (d, 2H), 7.65 (d, 2H), 7.58 (d, 1H), 7.52 (d, 3H), 4.74 (s, 1H), 4.63 (s, 1H), 4.35 (m, 2H), 3.84 (t, 1H), 3.66 (t, 1H), 3.50 (s, 1H), 3.30 (s, 2H), 3.02 (t, 2H), 2.90 (t, 1H), 2.80 (d, 7H), 1.06 (s, 2H), 1.70 (s, 2H) ppm; MS (ES) 551.29 (M+H);

1-(1,4-ethano-8-phenyl-1,2,3,4-tetrahydro-1,5-naphthyridin-6-yl)-$N^3$-(6-(cyclopentylamino)-5,6,7,8-tetrahydroquinoline-3-yl)-1H-1,2,4-triazole-3,5-diamine, compound #5, $^1$H NMR (DMSO-d$_6$, 300 MHz) 10.03 (s, 1H), 8.91 (s, 1H), 8.75 (d, 2H), 7.99 (s, 1H), 7.85 (s, 2H), 7.63 (d, 2H), 7.57 (s, 1H), 7.50 (d, 3H), 3.70 (s, 2H), 3.55 (m, 2H), 3.35 (d, 2H), 3.03 (s, 2H), 2.90 (m, 1H), 2.71 (s, 1H), 2.26 (m, 2H), 2.04 (s, 4H), 1.89 (t, 1H), 1.73 (d, 4H), 1.57 (s, 1.57) ppm; MS (ES) 548.28 (M+H);

1-(1,4-ethano-8-phenyl-1,2,3,4-tetrahydro-1,5-naphthyridin-6-yl)-$N^3$-(6-(cyclopentyl)-5,6,7,8-tetrahydro-1,6-naphthyridine-3-yl)-1H-1,2,4-triazole-3,5-diamine, compound #6, $^1$H NMR (DMSO-d$_6$, 300 MHz) 10.05 (s, 1H), 9.65 (s, 1H), 8.78 (s, 1H), 7.83 (d, 4H), 7.63 (s, 2H), 7.54 (m, 5H), 4.59 (s, 1H), 4.42 (s, 1H), 3.67 (m, 4H), 3.41 (m, 1H), 3.08 (m, 4H), 2.10 (s, 4H), 1.75 (m, 7H), 1.60 (s, 2H) ppm; MS (ES) 534.26 (M+H);

1-(6,9-ethano-4-phenyl-6,7,8,9-tetrahydro-5H-pyrido[3,2-c]azepin-2-yl)-$N^3$-(4-(4-(pyrrolidin-1-yl)piperidinyl)-3-fluorophenyl)-1H-1,2,4-triazole-3,5-diamine, compound #7, $^1$H-NMR (DMSO-d6, 300 MHz) 7.52 (m, 3H), 7.44 (m, 2H), 7.38 (m, 1H), 7.37 (m, 1H), 7.20 (m, 1H), 6.93 (m, 1H), 3.28-3.54 (m, 10H), 3.10 (m, 2H), 2.65 (m, 2H), 2.23 (m, 4H), 1.98-2.15 (m, 6H), 1.88 (m, 2H), 1.76 (m, 2H) ppm; MS (ES) 594.75 (M+H);

1-(1,4-ethano-8-(4-fluorophenyl)-1,2,3,4-tetrahydro-1,5-naphthyridin-6-yl)-$N^3$-(4-(4-(pyrrolidin-1-yl)piperidinyl)-3-fluorophenyl)-1H-1,2,4-triazole-3,5-diamine, compound #8, $^1$H-NMR (DMSO-d6, 300 MHz) 7.66-7.73 (m, 3H), 7.52 (s, 1H), 7.42 (m, 1H), 7.33 (m, 2H), 7.21 (m, 1H), 7.13 (t, 1H), 6.92 (t, 1H), 6.73 (m, 1H), 3.14 (m, 3H), 2.45-2.60 (m, 10H), 1.85-2.00 (m, 5H), 1.50-1.70 (m, 8H) ppm; MS (ES) 598.27 (M+H);

1-(1,4-ethano-8-(3-fluorophenyl)-1,2,3,4-tetrahydro-1,5-naphthyridin-6-yl)-$N^3$-(4-(4-(pyrrolidin-1-yl)piperidinyl)-3-fluorophenyl)-1H-1,2,4-triazole-3,5-diamine, compound #9, $^1$H-NMR (DMSO-d6, 300 MHz) 9.05 (s, 1H), 7.66 (m, 1H), 7.46-7.60 (m, 3H), 7.41 (m, 1H), 7.29 (m, 1H), 7.20 (m, 1H), 6.92 (m, 1H), 3.14 (m, 3H), 2.45-2.65 (m, 10H), 1.92 (m, 5H), 1.40-1.70 (m, 8H) ppm; MS (ES) 598.25 (M+H);

1-(1,4-ethano-8-(3-trifluoromethylphenyl)-1,2,3,4-tetrahydro-1,5-naphthyridin-6-yl)-$N^3$-(4-(4-(pyrrolidin-1-yl)piperidinyl)-3-fluorophenyl)-1H-1,2,4-triazole-3,5-diamine, compound #10, $^1$H-NMR (CDCl3-MeOD4, 300 MHz) 7.79 (m, 1H), 7.74 (m, 1H), 7.63 (m, 2H), 7.56 (m, 1H), 7.34 (m, 1H), 7.04 (m, 1H), 6.83 (t, 1H), 3.34 (m, 2H), 3.26 (m, 2H), 3.15 (m, 4H), 2.60 (m, 6H), 1.80-2.05 (m, 10H), 1.69 (m, 2H) ppm; MS (ES) 647.82 (M+H);

1-(1,4-ethano-8-(3-methoxyphenyl)-1,2,3,4-tetrahydro-1,5-naphthyridin-6-yl)-$N^3$-(4-(4-(pyrrolidin-1-yl)piperidinyl)-3-fluorophenyl)-1H-1,2,4-triazole-3,5-diamine, compound #11, $^1$H-NMR (DMSO-d6, 300 MHz) 9.05 (s, 1H), 7.66 (broad s, 2H), 7.52 (s, 1H), 7.36-7.50 (m, 2H), 7.20 (m, 2H), 7.02 (m, 1H), 6.92 (m, 1H), 3.81 (s, 3H), 3.34 (m, 2H), 3.14 (m, 3H), 2.52 (m, 8H), 1.91 (m, 5H), 1.40-1.70 (m, 8H) ppm; MS (ES) 610.28 (M+H);

1-(1,4-ethano-8-(2-methylphenyl)-1,2,3,4-tetrahydro-1,5-naphthyridin-6-yl)-$N^3$-(4-(4-(pyrrolidin-1-yl)piperidinyl)-3-fluorophenyl)-1H-1,2,4-triazole-3,5-diamine, compound #12, $^1$H-NMR (DMSO-d6, 300 MHz) 7.41 (m, 1H), 7.30-7.40 (m, 3H), 7.28 (m, 1H), 7.18-7.24 (m, 2H), 6.94 (t, 1H), 3.55 (m, 4H), 3.28 (m, 4H), 3.11 (m, 3H), 2.80 (m, 2H), 2.46 (m, 2H), 2.19 (s, 3H), 2.11 (m, 7H), 1.70-1.90 (m, 4H) ppm; MS (ES) 594.34 (M+H);

(7S)-1-(1,4-ethano-8-phenyl-1,2,3,4-tetrahydro-1,5-naphthyridin-6-yl)-$N^3$-(7-amino-6,7,8,9-tetrahydro-5H-benzo[7]annulene-2-yl)-1H-1,2,4-triazole-3,5-diamine, compound #26, $^1$H NMR (DMSO-d$_6$, 300 MHz): 8.80-9.00 (m, 1H), 7.60-7.76 (m, 4H), 7.40-7.58 (m, 4H), 7.25-7.38 (m, 2H), 6.88-7.00 (m, 1H), 3.02-3.16 (m, 2H), 2.86-2.99 (m, 1H), 2.59 (s br, 7H), 1.83-2.06 (m, 4H), 1.52-1.72 (m, 2H), 0.99-1.27 (m, 2H) ppm; MS (ES) 493.53 (M+H), 491.37 (M−H);

(7S)-1-(1,4-ethano-8-phenyl-1,2,3,4-tetrahydro-1,5-naphthyridin-6-yl)-$N^3$-(7-(dimethylamino)-6,7,8,9-tetrahydro-5H-benzo[7]annulen-2-yl)-1H-1,2,4-triazole-3,5-diamine, compound #36, MS (ES) 261.32 (M+2H/2);

(7S)-1-(1,4-ethano-8-phenyl-1,2,3,4-tetrahydro-1,5-naphthyridin-6-yl)-$N^3$-(7-(isopropylamino)-6,7,8,9-tetrahydro-5H-benzo[7]annulen-2-yl)-1H-1,2,4-triazole-3,5-diamine, compound #37, $^1$H NMR (DMSO-$d_6$, 300 MHz): 9.00 (s, 1H), 8.17 (s br, 2H), 7.72 (s br, 2H), 7.59-7.67 (m, 2H), 7.47-7.58 (m, 2H), 7.40 (d, J=8.3 Hz, 1H), 7.26 (s br, 1H), 7.00 (d, J=8.3 Hz, 1H), 3.20-3.60 (m, 5H), 2.56-2.97 (m, 8H), 2.14-2.32 (m, 2H), 1.92-2.14 (m, 2H), 1.63-1.81 (m, 2H), 1.23 (d, J=6.1 Hz, 6H) ppm; MS (ES) 535.12 (M+H), 533.30 (M−H);

(7S)-1-(1,4-ethano-8-phenyl-1,2,3,4-tetrahydro-1,5-naphthyridin-6-yl)-$N^3$-(7-(cyclobutylamino)-6,7,8,9-tetrahydro-5H-benzo[7]annulen-2-yl)-1H-1,2,4-triazole-3,5-diamine, compound #38, $^1$H NMR (DMSO-$d_6$, 300 MHz): 9.00 (s, 1H), 8.63 (s br, 2H), 7.72 (s br, 2H), 7.59-7.67 (m, 2H), 7.53 (s, 4H), 7.39 (d, J=8.0 Hz, 1H), 7.26 (s br, 1H), 6.99 (d, J=8.3 Hz, 1H), 3.74-3.93 (m, 1H), 3.52 (s br, 1H), 3.14-3.43 (m, 3H), 2.54-2.97 (m, 6H), 1.95-2.28 (m, 8H), 1.60-1.87 (m, 4H), 1.11-1.40 (m, 2H) ppm; MS (ES) 547.14 (M+H);

(7S)-1-(1,4-ethano-8-phenyl-1,2,3,4-tetrahydro-1,5-naphthyridin-6-yl)-$N^3$-(7-(dipropylamino)-6,7,8,9-tetrahydro-5H-benzo[7]annulen-2-yl)-1H-1,2,4-triazole-3,5-diamine, compound #39, $^1$H NMR (DMSO-$d_6$, 300 MHz): 8.86 (s, 1H), 8.14 (s, 1H), 7.61-7.71 (m, 3H), 7.40-7.58 (m, 4H), 7.34 (d, J=8.0 Hz, 1H), 7.27 (s, 1H), 6.95 (d, J=8.0 Hz, 1H), 3.00-3.16 (m, 2H), 2.71-2.85 (m, 2H), 2.53-2.70 (m, 4H), 2.27-2.43 (m, 5H), 1.84-2.05 (m, 5H), 1.52-1.71 (m, 2H), 1.27-1.45 (m, 4H), 1.07-1.27 (m, 2H), 0.81 (t, J=7.2 Hz, 6H) ppm; MS (ES) 577.24 (M+H), 576.52 (M);

(7S)-1-(1,4-ethano-8-phenyl-1,2,3,4-tetrahydro-1,5-naphthyridin-6-yl)-$N^3$-(7-(isobutylamino)-6,7,8,9-tetrahydro-5H-benzo[7]annulen-2-yl)-1H-1,2,4-triazole-3,5-diamine, compound #40, $^1$H NMR (DMSO-$d_6$, 300 MHz): 8.88 (s, 1H), 8.26 (s, 1H), 7.61-7.78 (m, 4H), 7.40-7.60 (m, 4H), 7.35 (d, J=8.0 Hz, 1H), 7.27 (s, 1H), 6.95 (d, J=8.3 Hz, 1H), 3.01-3.16 (m, 7H), 2.76-2.90 (m, 1H), 2.54-2.72 (m, 5H), 2.16-2.31 (m, 1H), 1.84-2.13 (m, 4H), 1.52-1.77 (m, 3H), 1.08-1.35 (m, 2H), 0.88 (d, J=6.6 Hz, 6H) ppm; MS (ES) 549.16 (M+H);

(7S)-1-(1,4-ethano-8-phenyl-1,2,3,4-tetrahydro-1,5-naphthyridin-6-yl)-$N^3$-(7-(diisobutylamino)-6,7,8,9-tetrahydro-5H-benzo[7]annulen-2-yl)-1H-1,2,4-triazole-3,5-diamine, compound #41, $^1$H NMR (DMSO-$d_6$, 300 MHz): 8.88 (s, 1H), 7.65 (s br, 3H), 7.39-7.59 (m, 5H), 7.34 (d, J=8.3 Hz, 1H), 7.25 (s, 1H), 6.94 (d, J=8.0 Hz, 1H), 2.99-3.17 (m, 4H), 2.52-2.69 (m, 5H), 1.85-2.09 (m, 9H), 1.48-1.71 (m, 4H), 0.98-1.21 (m, 2H), 0.80 (d, J=6.3 Hz, 12H) ppm; MS (ES) 605.26 (M+H);

1-(4-chloro-5,8-ethano-5,6,7,8-tetrahydrophthalazine-1-yl)-$N^3$-(4-(4-(pyrrolidin-1-yl)piperidinyl)-3-fluorophenyl)-1H-1,2,4-triazole-3,5-diamine, compound #13, $^1$H NMR (DMSO-$d_6$, 300 MHz) 9.18 (s, 1H, NH), 7.25 (d, 1H), 7.12 (s, 2H), 7.05 (d, 1H), 6.90 (t, 1H), 4.12 (s, 1H), 3.22-3.04 (m, 9H), 2.62-2.22 (m, 4H), 2.04-1.82 (m, 2H), 1.88-1.21 (m, 11H) ppm; MS (ES) 538.20 (M+H);

1-(4-chloro-5,8-ethano-5,6,7,8-tetrahydrophthalazine-1-yl)-$N^5$-(4-(4-(pyrrolidin-1-yl)piperidinyl)-3-fluorophenyl)-1H-1,2,4-triazole-3,5-diamine, compound #14, $^1$H NMR (DMSO-$d_6$, 300 MHz) 9.71 (s, 1H, NH), 7.71 (m, 1H), 7.08 (d, 1H), 6.95 (t, 1H), 5.75 (s, 2H, $NH_2$), 4.05 (d, 1H), 4.01 (s, 1H), 3.44-3.17 (m, 9H), 2.71-2.41 (m, 5H), 2.08-1.18 (m, 11H) ppm; MS (ES) 538.66 (M+H), 536.48 (M−H);

(3S)-1-(4-chloro-5,8-ethano-5,6,7,8-tetrahydrophthalazine-1-yl)-$N^3$-(6-(4-(cyclopropylmethyl)-3-methylpiperazin-1-yl)pyridin-3-yl)-1H-1,2,4-triazole-3,5-diamine, compound #20, $^1$H NMR (DMSO-$d_6$, 300 MHz) 8.84 (s, 1H, NH), 8.41 (s, 1H), 7.81 (d, 1H), 7.10 (s br, 2H, $NH_2$), 6.78 (d, 1H), 4.21 (s, 1H), 3.79 (t, 2H), 3.38-3.30 (m, 4H), 3.02 (d, 1H), 2.92 (t, 1H), 2.58-2.24 (m, 3H), 2.05 (m, 1H), 1.86 (d, 4H), 1.37 (d, 4H), 0.81 (m, 1H), 0.43 (m, 2H) ppm; MS (ES) 521.22 (M+H);

1-(4-chloro-5,8-ethano-5,6,7,8-tetrahydrophthalazine-1-yl)-$N^3$-(7-(pyrrolidin-1-yl)-6,7,8,9-tetrahydro-5H-benzo[7]annulen-2-yl)-1H-1,2,4-triazole-3,5-diamine, compound #27, $^1$H NMR (DMSO-$d_6$, 300 MHz): 8.96 (s, 1H), 7.39 (s, 1H), 7.24 (s br, 2H), 7.07-7.18 (m, 1H), 6.72 (d, J=7.7 Hz, 1H), 4.38 (s br, 1H), 3.36-3.43 (m, 1H), 2.73-2.96 (m, 2H), 2.42 (s br, 2H), 1.84 (s br, 7H), 1.65 (s br, 5H), 1.37 (s br, 7H) ppm; MS (ES) 505.18 (M);

1-(4-phenyl-5,6,7,8-tetrahydroquinazoline-2-yl)-$N^3$-(4-(4-(pyrrolidin-1-yl)piperidinyl)-3-fluorophenyl)-1H-1,2,4-triazole-3,5-diamine, compound #42, $^1$H-NMR (DMSO-d6, 300 MHz) 9.14 (s, 1H), 7.65-7.62 (m, 3H), 7.54-7.50 (m, 5H), 7.15 (d, 1H), 6.94 (t, 1H), 3.53 (m, 2H), 3.30-3.28 (m, 2H), 3.24-3.16 (m, 1H), 3.14-3.00 (m, 2H), 2.95-2.91 (m, 2H), 2.69-2.58 (m, 4H), 2.16-2.10 (m, 4H), 1.86 (m, 4H), 1.70 (m, 4H) ppm; MS (ES) 554.12 (M+H); and 1-(5,8-ethano-4-phenyl-5,6,7,8-tetrahydropyrido[3,2-d]pyrimidin-2-yl)-$N^3$-(4-(4-(pyrrolidin-1-yl)piperidinyl)-3-fluorophenyl)-1H-1,2,4-triazole-3,5-diamine, compound #43, $^1$H-NMR (DMSO-d6, 300 MHz) 9.19 (s, 1H), 8.25-8.21 (m, 2H), 7.75 (br. s, 2H), 7.66 (d, 1H), 7.54-7.52 (m, 3H), 7.20 (d, 1H), 6.97 (t, 1H), 3.32-3.30 (m, 4H), 3.18-3.04 (m, 8H), 2.71-2.59 (m, 5H), 2.27-2.25 (m, 1H), 2.16-2.02 (m, 4H), 1.88-1.86 (m, 2H), 1.76-1.74 (m, 2H) ppm; MS (ES) 581.60 (M+H).

SYNTHETIC EXAMPLE 4

Synthesis of 1-(4-(pyridin-4-yl)-5,8-ethano-5,6,7,8-tetrahydrophthalazine-1-yl)-$N^3$-(4-(4-(pyrrolidin-1-yl)piperidinyl)-3-fluorophenyl)-1H-1,2,4-triazole-3,5-diamine 1-(4-Chloro-5,8-ethano-5,6,7,8-tetrahydrophthalazine-1-yl)-$N^3$-(4-(4-(pyrrolidin-1-yl)piperidinyl)-3-fluorophenyl)-1H-1,2,4-triazole-3,5-diamine (50 mg, 0.09 mmol) and 4-pyridineboronic acid (16.4 mg, 0.135 mmol) were mixed with DME/EtOH/$H_2O$ (7/3/2) (2.5 mL). Then 0.5 mL of a 2M $Na_2CO_3$ solution and $PdCl_2(PPh_3)_2$ (10 mg) was added. The reaction mixture was heated using a microwave for 15 min at 150° C. The crude product was decanted from the solids ($Na_2CO_3$) and filtered through a glass frit (M). The solvents were evaporated and the crude product was subjected to reverse phase HPLC purification to give the desired product, 1-(4-(pyridin-4-yl)-5,8-ethano-5,6,7,8-tetrahydrophthalazine-1-yl)-$N^3$-(4-(4-(pyrrolidin-1-yl)piperidinyl)-3-fluorophenyl)-1H-1,2,4-triazole-3,5-diamine (29.8 mg, 57%), compound #18; $^1$H NMR (DMSO-$d_6$, 300 MHz) 9.21 (s, 1H, NH), 8.79 (d, 1H), 8.15 9 (s br, 2H), 7.63 (d, 1H), 7.58 (d, 1H), 7.23 (s, 2H), 7.13 (d, 1H), 6.94 (t, 1H), 4.22 (s, 1H), 3.61-3.06 (m, 9H), 2.63-2.41 (m, 6H), 2.18-1.19 (m 11H) ppm; MS (ES) 581.27 (M+H), 679.42 (M−H).

SYNTHETIC EXAMPLE 5

In a similar manner as described above in Synthetic Example 4, utilizing the appropriately substituted starting materials, substituted boronic acids and reagents, the following compounds were prepared:

1-(4-(2-chlorophenyl)-5,8-ethano-5,6,7,8-tetrahydrophthalazine-1-yl)-N$^3$-(4-(4-(pyrrolidin-1-yl)piperidinyl)-3-fluorophenyl)-1H-1,2,4-triazole-3,5-diamine, compound #15, $^1$H NMR (DMSO-d$_6$, 300 MHz) 9.13 (s, 1H, NH), 7.68-7.48 (m, 5H), 7.38 (s, 2H), 7.18 (d, 1H), 6.95 (t, 1H), 4.31 (s, 1H), 3.52 (s br, 2H), 3.38-3.01 (m, 8H), 2.71-2.42 (m, 8H), 2.18-1.17 (m, 9H) ppm; MS (ES) 614.29 (M+H), 612.30 (M−H);

1-(4-(3-cyanophenyl)-5,8-ethano-5,6,7,8-tetrahydrophthalazine-1-yl)-N$^3$-(4-(4-(pyrrolidin-1-yl)piperidinyl)-3-fluorophenyl)-1H-1,2,4-triazole-3,5-diamine, compound #16, $^1$H NMR (DMSO-d$_6$, 300 MHz) 9.10 (s, 1H, NH), 8.11 (s, 1H), 8.04-7.95 (m, 2H), 7.77 (m, 1H), 7.57 (d, 1H), 7.25 (s, 2H), 7.10 (d, 1H), 6.91 (t, 1H), 4.14 (s, 1H), 3.18 (m, 4H), 2.82 (m, 4H), 2.55 (m, 6H), 2.01-1.38 (m, 12H) ppm; MS (ES) 605.23 (M+H), 603.40 (M−H);

1-(4-(benzo[d][1,3]dioxol-5-yl)-5,8-ethano-5,6,7,8-tetrahydrophthalazine-1-yl)-N$^3$-(4-(4-(pyrrolidin-1-yl)piperidinyl)-3-fluorophenyl)-1H-1,2,4-triazole-3,5-diamine, compound #17, $^1$H NMR (DMSO-d$_6$, 300 MHz) 9.17 (s, 1H), 7.55 (d, J=15.4 Hz, 2H), 7.02-7.29 (m, 5H), 6.93 (t, 1H), 6.52 (s br, 1H), 6.12 (s, 2H), 4.19 (s br, 1H), 3.00-3.16 (m, 4H), 2.76-2.95 (m, 2H), 2.55-2.70 (m, 2H), 1.97-2.15 (m, 2H), 1.85 (s br, 9H), 1.55-1.73 (m, 3H), 1.30-1.52 (m, 4H) ppm; MS (ES) 624.30 (M+H), 622.45 (M−H);

1-(4-(3-methylphenyl)-5,8-ethano-5,6,7,8-tetrahydrophthalazine-1-yl)-N$^3$-(4-(4-(pyrrolidin-1-yl)piperidinyl)-3-fluorophenyl)-1H-1,2,4-triazole-3,5-diamine, compound #19, MS (ES) 594.33 (M+H), 593.61 (M);

(3S)-1-(4-phenyl-5,8-ethano-5,6,7,8-tetrahydrophthalazine-1-yl)-N$^3$-(6-(4-(cyclopropylmethyl)-3-methylpiperazin-1-yl)pyridin-3-yl)-1H-1,2,4-triazole-3,5-diamine, compound #21, $^1$H NMR (DMSO-d$_6$, 300 MHz) 8.89 (s, 1H, NH), 8.32 (s, 1H), 7.82 (d, 1H), 7.62-7.52 (m, 5H), 7.11 (s, 2H, NH$_2$), 6.78 (d, 1H), 4.21 (s, 1H), 3.78 (t, 2H), 3.22 (s, 1H), 3.04 (d, 1H), 2.84 (t, 1H), 2.61-2.38 (m, 7H), 2.11 (q, 1H), 1.82 (m, 4H), 1.40 (s br, 4H), 1.10 (d, 2H), 0.82 (m, 1H), 0.43 (m, 2H) ppm; MS (ES) 563.25 (M+H), 561.26 (M−H);

(3S)-1-(4-(2-chlorophenyl)-5,8-ethano-5,6,7,8-tetrahydrophthalazine-1-yl)-N$^3$-(6-(4-(cyclopropylmethyl)-3-methylpiperazin-1-yl)pyridin-3-yl)-1H-1,2,4-triazole-3,5-diamine, compound #22, $^1$H NMR (DMSO-d$_6$, 300 MHz) 8.92 (s, 1H, NH), 8.35 (s, 1H), 8.18 (s, 1H), 7.82 (d, 1H), 7.64-7.45 (m, 3H), 7.35 (s, 2H, NH$_2$), 6.79 (d, 1H), 4.34 (s, 1H), 3.82 (t, 2H), 3.20 (d, 1H), 2.96 (t, 1H), 2.71-2.41 (m, 7H), 2.23 (q, 1H), 1.80 (m, 4H), 1.40 (s br, 4H), 1.41-1.01 (m, 3H), 0.88 (m, 1H), 0.48 (m, 2H) ppm; MS (ES) 597.19 (M+H), 596.66 (M−H);

(3S)-1-(4-(3-methylphenyl)-5,8-ethano-5,6,7,8-tetrahydrophthalazine-1-yl)-N$^3$-(6-(4-(cyclopropylmethyl)-3-methylpiperazin-1-yl)pyridin-3-yl)-1H-1,2,4-triazole-3,5-diamine, compound #23, $^1$H NMR (DMSO-d$_6$, 300 MHz) 8.84 (s, 1H, NH), 8.37 (s, 1H), 8.16 (s, 1H), 7.81 (d, 1H), 7.43-7.23 (m, 3H), 7.19 (s, 2H, NH$_2$), 6.78 (d, 1H), 4.20 (s, 1H), 3.81 (t, 2H), 3.22 (s br, 1H), 3.08 (d, 2H), 2.96 (t, 1H), 2.75-2.37 (m, 8H), 2.20 (q, 1H), 1.83 (m, 4H), 1.41 (s br, 4H), 1.05 (d, 2H), 0.82 (m, 1H), 0.43 (m, 2H), 0.06 m, 1H) ppm; MS (ES) 577.27 (M+H), 576.26 (M);

(3S)-1-(4-(pyridin-4-yl)-5,8-ethano-5,6,7,8-tetrahydrophthalazine-1-yl)-N$^3$-(6-(4-(cyclopropylmethyl)-3-methylpiperazin-1-yl)pyridin-3-yl)-1H-1,2,4-triazole-3,5-diamine, compound #24, $^1$H NMR (DMSO-d$_6$, 300 MHz) 8.89 (s, 1H), 8.77 (d, J=5.8 Hz, 2H), 8.31 (d, J=2.5 Hz, 1H), 8.16 (s, 1H), 7.78-7.89 (m, 1H), 7.64 (d, J=6.1 Hz, 2H), 7.28 (s br, 2H), 6.77 (d, 1H), 4.27 (s br, 2H), 3.82 (t, J=11.4 Hz, 3H), 3.22 (s br, 1H), 3.09 (d, J=11.6 Hz, 1H), 2.89 (t, 1H), 2.32-2.69 (m, 6H), 2.18 (dd, J=12.9, 6.6 Hz, 1H), 1.73-1.95 (m, 4H), 1.28-1.49 (m, 4H), 1.04 (d, J=5.8 Hz, 3H), 0.78-0.91 (m, 1H), 0.39-0.54 (m, 2H), 0.02-0.18 (m, 2H) ppm; MS (ES) 564.23 (M+H);

1-(4-phenyl-5,8-ethano-5,6,7,8-tetrahydrophthalazine-1-yl)-N$^3$-(7-(pyrrolidin-1-yl)-6,7,8,9-tetrahydro-5H-benzo[7]annulene-2-yl)-1H-1,2,4-triazole-3,5-diamine, compound #28, $^1$H NMR (DMSO-d$_6$, 300 MHz): 9.71 (s br, 1H), 9.10 (s, 1H), 7.45-7.74 (m, 6H), 7.26-7.43 (m, 1H), 7.22 (d, J=8.3 Hz, 1H), 7.00 (d, 1H), 4.34 (s br, 1H), 3.25 (s, 1H), 2.99-3.18 (m, 2H), 2.57-2.85 (m, 4H), 2.43-2.56 (m, 1H), 2.17-2.38 (m, 2H), 1.67-2.03 (m, 10H), 1.22-1.58 (m, 6H) ppm; MS (ES) 547.26 (M+H);

1-(4-(2-chlorophenyl)-5,8-ethano-5,6,7,8-tetrahydrophthalazine-1-yl)-N$^3$-(7-(pyrrolidin-1-yl)-6,7,8,9-tetrahydro-5H-benzo[7]annulene-2-yl)-1H-1,2,4-triazole-3,5-diamine, compound #29, $^1$H NMR (DMSO-d$_6$, 300 MHz): 9.55 (s br, 1H), 9.10 (s, 1H), 7.61-7.72 (m, 1H), 7.46-7.62 (m, 4H), 7.37 (s br, 1H), 7.15-7.28 (m, 1H), 7.01 (d, 1H), 4.37-4.51 (m, 1H), 2.98-3.22 (m, 2H), 2.57-2.82 (m, 5H), 2.18-2.37 (m, 2H), 1.67-2.04 (m, 10H), 1.14-1.64 (m, 7H) ppm; MS (ES) 581.25 (M+H);

1-(4-(3-methylphenyl)-5,8-ethano-5,6,7,8-tetrahydrophthalazine-1-yl)-N$^3$-(7-(pyrrolidin-1-yl)-6,7,8,9-tetrahydro-5H-benzo[7]annulene-2-yl)-1H-1,2,4-triazole-3,5-diamine, compound #30, $^1$H NMR (DMSO-d$_6$, 300 MHz): 9.71 (s br, 1H), 9.09 (s, 1H), 7.27-7.59 (m, 6H), 7.16-7.27 (m, 1H), 7.00 (d, 1H), 4.33 (s, 1H), 3.20-3.31 (m, 1H), 3.00-3.20 (m, 2H), 2.57-2.87 (m, 4H), 2.41 (s, 3H), 2.11-2.36 (m, 2H), 1.69-2.04 (m, 10H), 1.23-1.56 (m, 7H) ppm; MS (ES) 561.30 (M+H);

1-(4-(3-cyanophenyl)-5,8-ethano-5,6,7,8-tetrahydrophthalazine-1-yl)-N$^3$-(7-(pyrrolidin-1-yl)-6,7,8,9-tetrahydro-5H-benzo[7]annulene-2-yl)-1H-1,2,4-triazole-3,5-diamine, compound #31, $^1$H NMR (DMSO-d$_6$, 300 MHz): 9.84 (s br, 1H), 9.16 (s, 1H), 8.09 (s, 1H), 8.01 (d, 1H), 7.95 (d, 1H), 7.72-7.88 (m, 1H), 6.98 (d, 1H), 4.39 (s br, 1H), 2.96-3.25 (m, 3H), 2.55-2.84 (m, 4H), 2.43-2.55 (m, 1H), 2.17-2.39 (m, 2H), 1.69-2.03 (m, 10H), 1.24-1.55 (m, 6H) ppm; MS (ES) 572.27 (M+H);

1-(4-(2-ethoxy-5-methylphenyl)-5,8-ethano-5,6,7,8-tetrahydrophthalazine-1-yl)-N$^3$-(7-(pyrrolidin-1-yl)-6,7,8,9-tetrahydro-5H-benzo[7]annulene-2-yl)-1H-1,2,4-triazole-3,5-diamine, compound #32, $^1$H NMR (DMSO-d$_6$, 300 MHz): 9.52 (s br, 1H), 9.03 (s, 1H), 7.44-7.55 (m, 1H), 7.38 (s br, 1H), 7.10-7.33 (m, 2H), 6.95-7.10 (m, 1H), 6.86 (d, 1H), 4.35 (s br, 1H), 2.95-3.16 (m, 3H), 2.56-2.87 (m, 4H), 2.28 (m, 3H), 2.19 (m, 4H), 1.65-2.02 (m, 10H), 1.47-1.64 (m, 2H), 1.31 (m, 5H), 1.04-1.21 (m, 3H) ppm; MS (ES) 605.31 (M+H);

1-(4-(4-fluoro-2-methylphenyl)-5,8-ethano-5,6,7,8-tetrahydrophthalazine-1-yl)-N$^3$-(7-(pyrrolidin-1-yl)-6,7,8,9-tetrahydro-5H-benzo[7]annulene-2-yl)-1H-1,2,4-triazole-3, 5-diamine, compound #33, $^1$H NMR (DMSO-d$_6$, 300 MHz): 9.76 (s br, 1H), 9.14 (s, 1H), 7.48 (s br, 2H), 7.10-7.36 (m, 4H), 6.95-7.04 (m, 1H), 4.27-4.45 (m, 1H), 2.98-3.22 (m, 2H), 2.57-2.84 (m, 5H), 2.42-2.55 (m, 1H), 2.20-2.39 (m, 2H), 2.14 (s, 3H), 1.69-2.02 (m, 9H), 1.21-1.58 (m, 7H) ppm; MS (ES) 579.30 (M+H), 577.31 (M−H); and 1-(4-(pyridin-4-yl)-5,8-ethano-5,6,7,8-tetrahydrophthalazine-1-yl)-N$^3$-(7-(pyrrolidin-1-yl)-6,7,8,9-tetrahydro-5H-benzo[7]annulene-2-yl)-1H-1,2,4-triazole-3,5-diamine, compound #34, $^1$H NMR (DMSO-d$_6$, 300 MHz): 9.62 (s br, 1H), 9.10 (s, 1H), 8.94 (d, 2H), 7.99 (d, 2H), 7.48 (s, 1H), 7.21 (d, 1H), 7.00 (d, 2H), 4.36-4.48 (m, 1H), 3.30-3.53 (m, 4H), 2.98-3.16 (m, 2H), 2.56-2.81 (m, 4H), 2.42-2.51 (m, 2H), 2.15-2.38 (m, 2H), 1.71-2.04 (m, 8H), 1.26-1.54 (m, 4H) ppm; MS (ES) 548.24 (M+H), 546.22 (M−H).

BIOLOGICAL EXAMPLE 1

Phospho-Akt in-Cell Western Assay

The compounds of the invention were tested in the following assay for their ability to inhibit Axl activity.

Reagents and Buffers:

Cell culture plate: 96 well assay plate (Corning 3610), white, clear bottom, tissue-culture treated.

Cells: Hela cells.

Starvation medium: For Axl stimulation: 0.5% FCS (fetal calf serum) in DMEM, plus Axl/Fc (extracellular domain of AXL fused to immunoglobulin Fc region) (R&D, 154-AL) 500 ng/mL.

For EGF (epidermal growth factor) stimulation: 0.5% FCS in DMEM (Dulbecco's modified Eagles medium).

Poly-L-Lysine 0.01% solution (the working solution): 10 µg/ml, dilute In PBS (phosphate buffered saline).

Axl antibody cross-linking:
  1$^{st}$: Mouse anti-Axl (R&D, MAB154).
  2$^{nd}$: Biotin-SP-conjugated AffiniPure goat anti-mouse IgG (H+L) (Jackson ImmunoResearch #115-065-003).

Fixing buffer: 4% formaldehyde in PBS.

Wash buffer: 0.1% TritonX-100 in PBS.

Quenching buffer: 3% H$_2$O$_2$, 0.1% Azide in wash buffer, Azide and hydrogen peroxide (H$_2$O$_2$) are added fresh.

Blocking buffer: 5% BSA in TBST (tris buffered saline plus 0.1% Tween 20).

Primary antibody: Rabbit anti-human Phospho-Akt antibody (Cell Signaling 9271): 1×250 diluted in blocking buffer.

Secondary antibody: HRP (horse radish peroxidase)-conjugated Goat anti-Rabbit secondary, stock solution: Jackson ImmunoResearch (Goat anti-Rabbit HRP, #111-035-144) 1:1 diluted in glycerol, store at −20° C. The working solution: 1×2000 dilution of stock in blocking buffer.

Chemiluminescent working solution (Pierce, 37030): SuperSignal ELISA (enzyme linked immunosorbant assay) Pico Chemiluminescent substrate.

Crystal Violet solution: Stock: 2.5% Crystal violet in methanol, filtered and kept at ambient temperature. The working solution: dilute the stock 1:20 with PBS immediately before use.

10% SDS: working solution: 5% SDS (sodium dodecylsulfate), diluted in PBS

Methods:

Day 1:

A 96 well TC (tissue culture treated) plate was coated with 10 µg/mL poly-L-Lysine at 37° C. for 30 min, washed twice with PBS, and air-dried for 5 minutes before cells were added. Hela cells were seeded at 10,000 cells/well and the cells were starved in 100 µL starvation medium containing Axl/Fc for 24 hrs.

Day 2:

The cells were pre-treated with test compounds by adding 100 µL of 2× test compound to the starvation medium on the cells. The cells were incubated at 37° C. for 1 hr before stimulation.

The cells were stimulated by Axl-antibody cross-linking as follows: A 5×1$^{st}$/2$^{nd}$ Axl antibody mixture was made (37.5 µg/mL 1$^{st}$/100 µg/mL 2$^{nd}$) in starvation medium and nutated at 4° C. with thorough mixing for 1-2 hours for clustering. The resulting mix was warmed to 37° C. 50 µL of 5× Axl 1$^{st}$/2$^{nd}$ of antibody cluster was added to the cells and the cells were incubated at 37° C. for 5 min.

After 5 minutes stimulation, the plate was flicked to remove medium and the plate was tapped onto paper towels. Formaldehyde (4.0% in PBS, 100 µL) was added to fix the cells and the cells were incubated at ambient temperature for 20 min without shaking.

The cells were washed with a plate washer buffer to remove the formaldehyde solution. The plate was flicked to removed excess wash buffer and tapped onto paper towels. Quenching buffer (100 µL) was added to each well and the cells were incubated at ambient temperature for 20 minutes without shaking.

The cells were washed with a plate washer buffer to remove the quenching buffer. Blocking buffer (100 µL) was added and the cells were incubated at ambient temperature for at least an hour with gentle shaking.

The cells were washed with a plate washer buffer and diluted primary antibody (50 µL) was added to each well (blocking buffer was added to the negative control wells instead). The plates were incubated overnight at 4° C. with gentle shaking.

Day 3:

The wash buffer was removed, diluted secondary antibody (100 µL) was added, and the cells were incubated at ambient temperature for 1 hour with gentle shaking. During the incubation, the chemiluminescent reagent was brought to ambient temperature.

The secondary antibody was removed by washing the cells 1× with wash buffer, 1× with PBS by plate washer. The PBS was removed from the plate and the chemiluminescent reagent (80 µL: 40 µL A and 40 µL B) was added to each well at ambient temperature.

The resulting chemiluminescence was read with a Luminomitor within 10 minutes to minimize changes in signal intensity. After reading the chemiluminescence, the cells were washed 1× with wash buffer and 1× with PBS by plate washer. The plate was tapped onto paper towels to remove excess liquid from wells and air-dried at ambient temperature for 5 minutes.

Crystal Violet working solution (60 µL) was added to each well and the cells were incubated at ambient temperature for 30 min. The crystal violet solution was removed, and the wells were rinsed with PBS, then washed 3× with PBS (200 µL) for 5 minutes each.

5% SDS solution (70 µL) was added to each well and the cells were incubated on a shaker for 30 min at ambient temperature.

The absorbance was read at 590 nM on a Wallac photospec. The 590 nM readings indicated the relative cell number in each well. This relative cell number was then used to normalize each luminescence reading.

The results of the ability of the compounds of the invention to inhibit Axl activity, when tested in the above assay, are shown in the following Tables wherein the level of activity (i.e., the $IC_{50}$) for each compound is indicated in each Table. The compound numbers in the Tables referred to the compounds disclosed herein as being prepared by the methods disclosed herein:

TABLE 1

(Ia)

| Cpd # | Compound Name | $R^1$ | $IC_{50}$ |
|---|---|---|---|
| 1 | 1-(1,4-ethano-8-phenyl-1,2,3,4-tetrahydro-1,5-naphthyridin-6-yl)-$N^3$-(6-amino-5,6,7,8-tetrahydroquinoline-3-yl)-1H-1,2,4-triazole-3,5-diamine | $H_2N$— | A |
| 3 | 1-(1,4-ethano-8-phenyl-1,2,3,4-tetrahydro-1,5-naphthyridin-6-yl)-$N^3$-(6-[(((dimethyl)amino)methyl)carbonylamino]-5,6,7,8-tetrahydroquinoline-3-yl)-1H-1,2,4-triazole-3,5-diamine | $(CH_3)_2NCH_2C(O)NH$— | A |
| 5 | 1-(1,4-ethano-8-phenyl-1,2,3,4-tetrahydro-1,5-naphthyridin-6-yl)-$N^3$-(6-(cyclopentylamino)-5,6,7,8-tetrahydroquinoline-3-yl)-1H-1,2,4-triazole-3,5-diamine | cyclopentyl-NH— | A |

$IC_{50}$ activity:
A = <1 μM
B = 1 to 10 μM
C = >10 to 20 μM
D = >20 μM

TABLE 2

(Ib)

| Cpd # | Compound Name | $R^2$ | $IC_{50}$ |
|---|---|---|---|
| 2 | 1-(1,4-ethano-8-phenyl-1,2,3,4-tetrahydro-1,5-naphthyridin-6-yl)-$N^3$-(5,6,7,8-tetrahydro-1,6-naphthryidine-3-yl)-1H-1,2,4-triazole-3,5-diamine | H— | A |
| 4 | 1-(1,4-ethano-8-phenyl-1,2,3,4-tetrahydro-1,5-naphthyridin-6-yl)-$N^3$-(6-[((dimethyl)amino)methylcarbonyl]-5,6,7,8-tetrahydro-1,6-naphthyridine-3-yl)-1H-1,2,4-triazole-3,5-diamine | $(CH_3)_2NCH_2C(O)$— | A |
| 6 | 1-(1,4-ethano-8-phenyl-1,2,3,4-tetrahydro-1,5-naphthyridin-6-yl)-$N^3$-(6-(cyclopentyl)-5,6,7,8-tetrahydro-1,6-naphthyridine-3-yl)-1H-1,2,4-triazole-3,5-diamine | cyclopentyl— | A |

$IC_{50}$ activity:
A = <1 μM
B = 1 to 10 μM
C = >10 to 20 μM
D = >20 μM

TABLE 3

(II)

| Cpd # | Compound Name | B | $R^6$ | $IC_{50}$ |
|---|---|---|---|---|
| 7 | 1-(6,9-ethano-4-phenyl-6,7,8,9-tetrahydro-5H-pyrido[3,2-c]azepin-2-yl)-$N^3$-(4-(4-(pyrrolidin-1-yl)piperidinyl)-3-fluorophenyl)-1H-1,2,4-triazole-3,5-diamine | —$CH_2$— | H | A |

TABLE 3-continued (II)

| Cpd # | Compound Name | B | R⁶ | IC₅₀ |
|---|---|---|---|---|
| 8 | 1-(1,4-ethano-8-(4-fluorophenyl)-1,2,3,4-tetrahydro-1,5-naphthyridin-6-yl)-N³-(4-(4-(pyrrolidin-1-yl)piperidinyl)-3-fluorophenyl)-1H-1,2,4-triazole-3,5-diamine | Direct bond | 4-F | A |
| 9 | 1-(1,4-ethano-8-(3-fluorophenyl)-1,2,3,4-tetrahydro-1,5-naphthyridin-6-yl)-N³-(4-(4-(pyrrolidin-1-yl)piperidinyl)-3-fluorophenyl)-1H-1,2,4-triazole-3,5-diamine | Direct bond | 3-F | F |
| 10 | 1-(1,4-ethano-8-(3-trifluoromethylphenyl)-1,2,3,4-tetrahydro-1,5-naphthyridin-6-yl)-N³-(4-(4-(pyrrolidin-1-yl)piperidinyl)-3-fluorophenyl)-1H-1,2,4-triazole-3,5-diamine | Direct bond | 3-CF₃ | A |
| 11 | 1-(1,4-ethano-8-(3-methoxyphenyl)-1,2,3,4-tetrahydro-1,5-naphthyridin-6-yl)-N³-(4-(4-(pyrrolidin-1-yl)piperidinyl)-3-fluorophenyl)-1H-1,2,4-triazole-3,5-diamine | Direct bond | 3-OCH₃ | A |
| 12 | 1-(1,4-ethano-8-(2-methylphenyl)-1,2,3,4-tetrahydro-1,5-naphthyridin-6-yl)-N³-(4-(4-(pyrrolidin-1-yl)piperidinyl)-3-fluorophenyl)-1H-1,2,4-triazole-3,5-diamine | Direct bond | 2-CH₃ | A |

IC₅₀ activity:
A = <1 μM
B = 1 to 10 μM
C = >10 to 20 μM
D = >20 μM

TABLE 4

(III)

| Cpd # | Compound Name | R⁷ | IC₅₀ |
|---|---|---|---|
| 25 | (7S)-1-(1,4-ethano-8-phenyl-1,2,3,4-tetrahydro-1,5-naphthyridin-6-yl)-N³-(7-(t-butoxycarbonyl-amino)-6,7,8,9-tetrahydro-5H-benzo[7]annulene-2-yl)-1H-1,2,4-triazole-3,5-diamine | t-Boc-NH- | NA |
| 26 | (7S)-1-(1,4-ethano-8-phenyl-1,2,3,4-tetrahydro-1,5-naphthyridin-6-yl)-N³-(7-amino-6,7,8,9-tetrahydro-5H-benzo[7]annulene-2-yl)-1H-1,2,4-triazole-3,5-diamine | H₂N- | A |
| 35 | (7S)-1-(1,4-ethano-8-phenyl-1,2,3,4-tetrahydro-1,5-naphthyridin-6-yl)-N³-(7-(diethylamino)-6,7,8,9-tetrahydro-5H-benzo[7]annulene-2-yl)-1,2,4-triazole-3,5-diamine | (H₃CCH₂)₂N- | A |
| 36 | (7S)-1-(1,4-ethano-8-phenyl-1,2,3,4-tetrahydro-1,5-naphthyridin-6-yl)-N³-(7-(dimethylamino)-6,7,8,9-tetrahydro-5H-benzo[7]annulene-2-yl)-1H-1,2,4-triazole-3,5-diamine | (H₃C)₂N- | D |
| 37 | (7S)-1-(1,4-ethano-8-phenyl-1,2,3,4-tetrahydro-1,5-naphthyridin-6-yl)-N³-(7-(isopropylamino)-6,7,8,9-tetrahydro-5H-benzo[7]annulene-2-yl)-1H-1,2,4-triazole-3,5-diamine | (H₃C)₂CH-NH- | A |
| 38 | (7S)-1-(1,4-ethano-8-phenyl-1,2,3,4-tetrahydro-1,5-naphthyridin-6-yl)-N³-(7-(cyclobutylamino)-6,7,8,9-tetrahydro-5H-benzo[7]annulene-2-yl)-1H-1,2,4-triazole-3,5-diamine | cyclobutyl-NH- | A |
| 39 | (7S)-1-(1,4-ethano-8-phenyl-1,2,3,4-tetrahydro-1,5-naphthyridin-6-yl)-N³-(7-(dipropylamino)-6,7,8,9-tetrahydro-5H-benzo[7]annulene-2-yl)-1H-1,2,4-triazole-3,5-diamine | (H₃CCH₂CH₂)₂N- | A |
| 40 | (7S)-1-(1,4-ethano-8-phenyl-1,2,3,4-tetrahydro-1,5-naphthyridin-6-yl)-N³-(7-(isobutylamino)-6,7,8,9-tetrahydro-5H-benzo[7]annulene-2-yl)-1H-1,2,4-triazole-3,5-diamine | (H₃C)₂CHCH₂-NH- | A |

TABLE 4-continued (III)

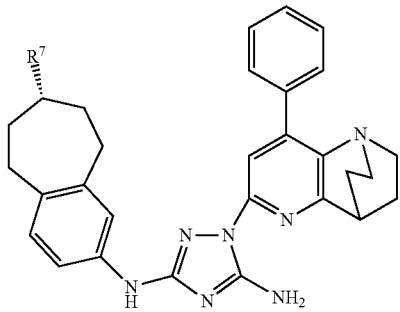

| Cpd # | Compound Name | R⁷ | IC$_{50}$ |
|---|---|---|---|
| 41 | (7S)-1-(1,4-ethano-8-phenyl-1,2,3,4-tetrahydro-1,5-naphthyridin-6-yl)-N³-(7-(diisobutylamino)-6,7,8,9-tetrahydro-5H-benzo[7]annulene-2-yl)-1H-1,2,4-triazole-3,5-diamine | 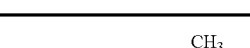 | A |

IC$_{50}$ activity:
A = <1 μM
B = 1 to 10 μM
C = >10 to 20 μM
D = >20 μM

TABLE 5

(IVa)

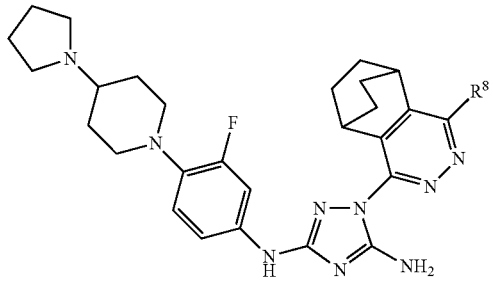

| Cpd # | Compound Name | R⁸ | IC$_{50}$ |
|---|---|---|---|
| 13 | 1-(4-chloro-5,8-ethano-5,6,7,8-tetrahydrophthalazine-1-yl)-N³-(4-(4-(pyrrolidin-1-yl)piperidinyl)-3-fluorophenyl)-1H-1,2,4-triazole-3,5-diamine | Cl | A |
| 15 | 1-(4-(2-chlorophenyl)-5,8-ethano-5,6,7,8-tetrahydrophthalazine-1-yl)-N³-(4-(4-(pyrrolidin-1-yl)piperidinyl)-3-fluorophenyl)-1H-1,2,4-triazole-3,5-diamine | 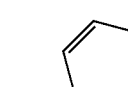 | A |
| 16 | 1-(4-(3-cyanophenyl)-5,8-ethano-5,6,7,8-tetrahydrophthalazine-1-yl)-N³-(4-(4-(pyrrolidin-1-yl)piperidinyl)-3-fluorophenyl)-1H-1,2,4-triazole-3,5-diamine | 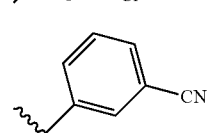 | A |

TABLE 5-continued (IVa)

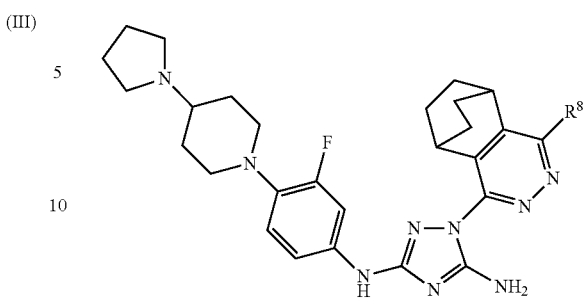

| Cpd # | Compound Name | R⁸ | IC$_{50}$ |
|---|---|---|---|
| 17 | 1-(4-(benzo[d][1,3]dioxol-5-yl)-5,8-ethano-5,6,7,8-tetrahydrophthalazine-1-yl)-N³-(4-(4-(pyrrolidin-1-yl)piperidinyl)-3-fluorophenyl)-1H-1,2,4-triazole-3,5-diamine | 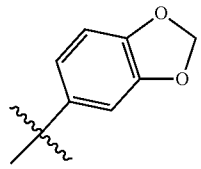 [SMILES: *c1ccc2c(c1)OCO2] | A |
| 18 | 1-(4-(pyridin-4-yl)-5,6,7,8-ethano-5,6,7,8-tetrahydrophthalazine-1-yl)-N³-(4-(4-(pyrrolidin-1-yl)piperidinyl)-3-fluorophenyl)-1H-1,2,4-triazole-3,5-diamine | 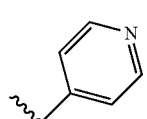 | A |
| 19 | 1-(4-(3-methylphenyl)-5,8-ethano-5,6,7,8-tetrahydro-phthalazine-1-yl)-N³-(4-(4-(pyrrolidin-1-yl)piperidinyl)-3-fluorophenyl)-1H-1,2,4-triazole-3,5-diamine | 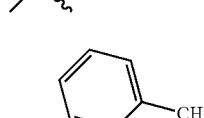 | B |

IC$_{50}$ activity:
A = <1 μM
B = 1 to 10 μM
C = >10 to 20 μM
D = >20 μM

TABLE 6

(IVb)

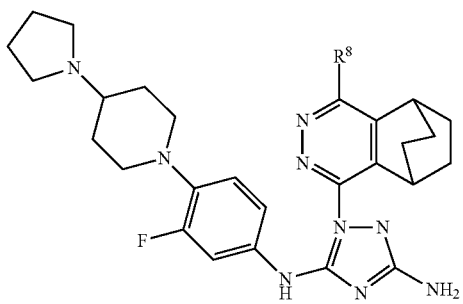

| Cpd # | Compound Name | R⁸ | IC$_{50}$ |
|---|---|---|---|
| 14 | 1-(4-chloro-5,8-ethano-5,6,7,8-tetrahydrophthalazine-1-yl)-N⁵-(4-(4-(pyrrolidin-1-yl)piperidinyl)-3-fluorophenyl)-1H-1,2,4-triazole-3,5-diamine | Cl | B |

IC$_{50}$ activity:
A = <1 μM
B = 1 to 10 μM
C = >10 to 20 μM
D = >20 μM

TABLE 7

(V)

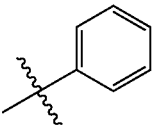

| Cpd # | Compound Name | R⁹ | IC₅₀ |
|---|---|---|---|
| 20 | (3S)-1-(4-chloro-5,8-ethano-5,6,7,8-tetrahydro-phthalazine-1-yl)-N³-(6-(4-(cyclopropylmethyl)-3-methylpiperazin-1-yl)pyridin-3-yl)-1H-1,2,4-triazole-3,5-diamine | Cl | A |
| 21 | (3S)-1-(4-phenyl-5,8-ethano-5,6,7,8-tetrahydro-phthalazine-1-yl)-N³-(6-(4-(cyclopropylmethyl)-3-methylpiperazin-1-yl)pyridin-3-yl)-1H-1,2,4-triazole-3,5-diamine | 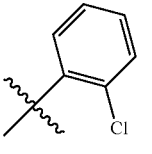 [SMILES: *c1ccccc1Cl] | B |
| 22 | (3S)-1-(4-(2-chlorophenyl)-5,8-ethano-5,6,7,8-tetrahydrophthalazine-1-yl)-N³-(6-(4-(cyclopropyl-methyl)-3-methyl-piperazin-1-yl)pyridin-3-yl)-1H-1,2,4-triazole-3,5-diamine | 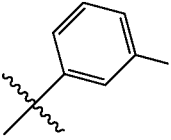 | A |
| 23 | (3S)-1-(4-(3-methylphenyl)-5,8-ethano-5,6,7,8-tetrahydrophthalazine-1-yl)-N³-(6-(4-(cyclopropylmethyl)-3-methylpiperazin-1-yl)pyridin-3-yl)-1H-1,2,4-triazole-3,5-diamine | 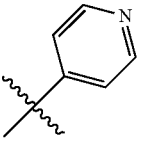 [SMILES: *c1ccncc1] | B |
| 24 | (3S)-1-(4-(pyridin-4-yl)-5,8-ethano-5,6,7,8-tetrahydrophthalazine-1-yl)-N³-(6-(4-(cyclopropyl-methyl)-3-methyl-piperazin-1-yl)pyridin-3-yl)-1H-1,2,4-triazole-3,5-diamine | 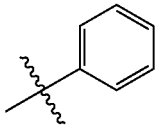 [SMILES: *c1ccccc1] | B |

IC₅₀ activity:

A = <1 μM

B = 1 to 10 μM

C = >10 to 20 μM

D = >20 μM

TABLE 8

(VI)

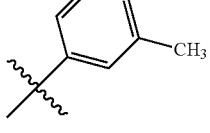

| Cpd # | Compound Name | R¹⁰ | IC₅₀ |
|---|---|---|---|
| 27 | 1-(4-chloro-5,8-ethano-5,6,7,8-tetrahydrophthalazine-1-yl)-N³-(7-(pyrrolidin-1-yl)-6,7,8,9-tetrahydro-5H-benzo[7]annulene-2-yl)-1H-1,2,4-triazole-3,5-diamine | Cl | A |
| 28 | 1-(4-phenyl-5,8-ethano-5,6,7,8-tetrahydrophthalazine-1-yl)-N³-(7-(pyrrolidin-1-yl)-6,7,8,9-tetrahydro-5H-benzo[7]annulene-2-yl)-1H-1,2,4-triazole-3,5-diamine | 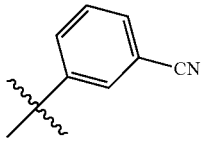 [SMILES: *c1cccc(C#N)c1] | A |
| 29 | 1-(4-(2-chlorophenyl)-5,8-ethano-5,6,7,8-tetrahydrophthalazine-1-yl)-N³-(7-(pyrrolidin-1-yl)-6,7,8,9-tetrahydro-5H-benzo[7]annulene-2-yl)-1H-1,2,4-triazole-3,5-diamine | | A |
| 30 | 1-(4-(3-methylphenyl)-5,8-ethano-5,6,7,8-tetrahydrophthalazine-1-yl)-N³-(7-(pyrrolidin-1-yl)-6,7,8,9-tetrahydro-5H-benzo[7]annulene-2-yl)-1H-1,2,4-triazole-3,5-diamine | 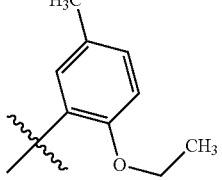 | A |
| 31 | 1-(4-(3-cyanophenyl)-5,8-ethano-5,6,7,8-tetrahydrophthalazine-1-yl)-N³-(7-(pyrrolidin-1-yl)-6,7,8,9-tetrahydro-5H-benzo[7]annulene-2-yl)-1H-1,2,4-triazole-3,5-diamine | | A |
| 32 | 1-(4-(2-ethoxy-5-methyl-phenyl)-5,8-ethano-5,6,7,8-tetrahydrophthalazine-1-yl)-N³-(7-(pyrrolidin-1-yl)-6,7,8,9-tetrahydro-5H-benzo[7]annulene-2-yl)-1H-1,2,4-triazole-3,5-diamine | | B |
| 33 | 1-(4-(4-fluoro-2-methyl-phenyl)-5,8-ethano-5,6,7,8-tetrahydrophthalazine-1-yl)-N³-(7-(pyrrolidin-1-yl)-6,7,8,9-tetrahydro-5H-benzo[7]annulene-2-yl)-1H-1,2,4-triazole-3,5-diamine | 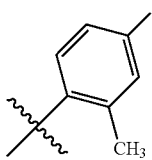 | A |

TABLE 8-continued

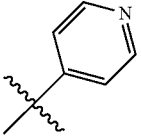 [SMILES: *c1ccncc1]

(VI)

| Cpd # | Compound Name | R[10] | IC$_{50}$ |
|---|---|---|---|
| 34 | 1-(4-(pyridin-4-yl)-5,8-ethano-5,6,7,8-tetrahydro-phthalazine-1-yl)-N³-(7-(pyrrolidin-1-yl)-6,7,8,9-tetrahydro-5H-benzo[7]annulene-2-yl)-1H-1,2,4-triazole-3,5-diamine | (pyridinyl structure) | A |

IC$_{50}$ activity:
A = <1 μM
B = 1 to 10 μM
C = >10 to 20 μM
D = >20 μM

TABLE 9

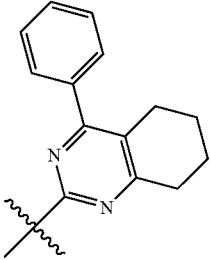 [SMILES: *c1nc2c(c(-c3ccccc3)n1)CCCC2]

(VII)

| Cpd # | Compound Name | R[11] | IC$_{50}$ |
|---|---|---|---|
| 42 | 1-(4-phenyl-5,6,7,8-tetrahydro-quinazoline-2-yl)-N³-(4-(4-(pyrrolidin-1-yl)piperidinyl)-3-fluorophenyl)-1H-1,2,4-triazole-3,5-diamine | (tetrahydroquinazoline structure) | A |

TABLE 9-continued

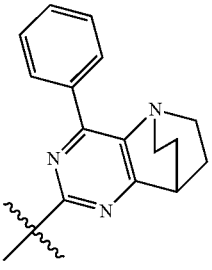 [SMILES: *c1nc(-c2ccccc2)c2c(n1)C1CCN2CC1]

(VII)

| Cpd # | Compound Name | R[11] | IC$_{50}$ |
|---|---|---|---|
| 43 | 1-(5,8-ethano-4-phenyl-5,6,7,8-tetrahydropyrido[3,2-d]pyrimidin-2-yl)-N³-(4-(4-(pyrrolidin-1-yl)piperidinyl)-3-fluorophenyl)-1H-1,2,4-triazole-3,5-diamine | (ethano-pyridopyrimidine structure) | A |

IC$_{50}$ activity:
A = <1 μM
B = 1 to 10 μM
C = >10 to 20 μM
D = >20 μM

All of the U.S. patents, U.S. patent application publications, U.S. patent applications, foreign patents, foreign patent applications and non-patent publications referred to in this specification and/or listed in the Application Data Sheet are incorporated herein by reference, in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (VI):

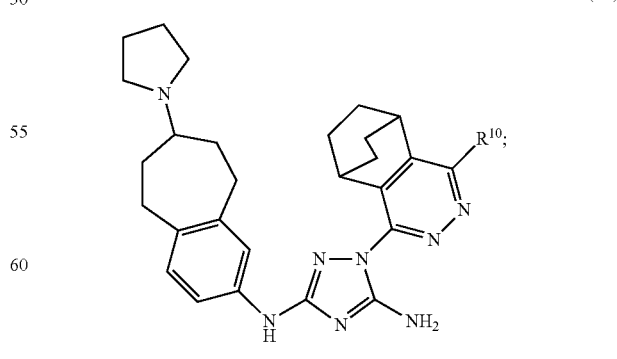

(VI)

wherein:
R[10] is selected from the group consisting of halo, pyridinyl and phenyl, where the phenyl is optionally substituted by one or more substituents selected from the group consisting of halo, cyano, alkoxy and alkyl;
as an isolated stereoisomer or a mixture thereof, or as a pharmaceutically acceptable salt thereof.

2. The compound of claim 1 selected from the group consisting of:
- 1-(4-chloro-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine;
- 1-(4-phenyl-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine;
- 1-(4-(2-chlorophenyl)-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine;
- 1-(4-(3-methylphenyl)-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine;
- 1-(4-(3-cyanophenyl)-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine;
- 1-(4-(2-ethoxy-5-methylphenyl)-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine;
- 1-(4-(4-fluoro-2-methylphenyl)-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine; and
- 1-(4-(pyridin-4-yl)-5,8-ethano-5,6,7,8-tetrahydrophthalazine-1-yl)-$N^3$-(7-(pyrrolidin-1-yl)-6,7,8,9-tetrahydro-5H-benzo[7]annulene-2-yl)-1H-1,2,4-triazole-3,5-diamine.

3. A pharmaceutical composition comprising a pharmaceutically acceptable excipient and a therapeutically effective amount of compound of claim 1, as an isolated stereoisomer or a mixture thereof, or as a pharmaceutically acceptable salt thereof.

4. A method of treating a disease or condition associated with Axl activity in a mammal, wherein the disease or condition is selected from the group consisting of rheumatoid arthritis, vascular disease, vascular injury, psoriasis, visual impairment due to macular degeneration, diabetic retinopathy, retinopathy of prematurity, kidney disease, osteoporosis, osteoarthritis, cataracts, breast carcinoma, renal carcinoma, endometrial carcinoma, ovarian carcinoma, thyroid carcinoma, non-small cell lung carcinoma, melanoma, prostate carcinoma, sarcoma, gastric cancer, uveal melanoma, myeloid leukemia, lymphoma and endometriosis, and wherein the method comprises administering to the mammal a therapeutically effective amount of a compound of claim 1, as an isolated stereoisomer or a mixture thereof, or a pharmaceutically acceptable salt thereof.

5. A method of inhibiting Axl activity in a cell, wherein the method comprises contacting the cell with an effective amount of a compound of claim 1, as an isolated stereoisomer or a mixture thereof, or as a pharmaceutically acceptable salt thereof.

* * * * *